US008540521B2

(12) United States Patent
Gee et al.

(10) Patent No.: US 8,540,521 B2
(45) Date of Patent: Sep. 24, 2013

(54) BENZOXAZOLE-BASED FLUORESCENT METAL ION INDICATORS

(75) Inventors: Kyle Gee, Springfield, OR (US); Vladimir Martin, Eugene, OR (US)

(73) Assignee: Life Technologies Corporation, Carlsbad, CA (US)

( * ) Notice: Subject to any disclaimer, the term of this patent is extended or adjusted under 35 U.S.C. 154(b) by 95 days.

(21) Appl. No.: 13/142,584

(22) PCT Filed: Dec. 29, 2009

(86) PCT No.: PCT/US2009/069696
§ 371 (c)(1),
(2), (4) Date: Sep. 2, 2011

(87) PCT Pub. No.: WO2010/078333
PCT Pub. Date: Jul. 8, 2010

(65) Prior Publication Data
US 2011/0306082 A1 Dec. 15, 2011

Related U.S. Application Data

(60) Provisional application No. 61/141,181, filed on Dec. 29, 2008.

(51) Int. Cl.
C12Q 1/02 (2006.01)
C07D 455/04 (2006.01)
C07D 417/04 (2006.01)
C07D 413/10 (2006.01)
C07D 263/56 (2006.01)
C07D 491/147 (2006.01)
G01N 21/75 (2006.01)

(52) U.S. Cl.
USPC ............ 439/29; 546/10; 546/12; 546/66; 546/94; 546/271.7; 548/108; 548/126; 548/159; 548/217; 548/224

(58) Field of Classification Search
None
See application file for complete search history.

(56) References Cited

U.S. PATENT DOCUMENTS

| 4,544,496 | A |   | 10/1985 | Claussen et al. |
|---|---|---|---|---|
| 4,603,209 | A |   | 7/1986 | Tsien et al. |
| 4,689,432 | A |   | 8/1987 | Tsien et al. |
| 5,141,627 | A |   | 8/1992 | Tsien |
| 5,453,517 | A | * | 9/1995 | Kuhn et al. ............ 549/227 |
| 5,454,517 | A |   | 10/1995 | Naemura |
| 5,501,980 | A |   | 3/1996 | Katerinopoulos et al. |
| 5,949,673 | A |   | 9/1999 | Struger et al. |

FOREIGN PATENT DOCUMENTS

| JP | 6207932 | 7/1994 |
|---|---|---|
| JP | 2509294 | 4/1996 |

OTHER PUBLICATIONS

Bourson, J., "Ion-Responsive Fluorescent Compounds. 2. Cation-Steered Intramolecular Charge Transfer in a Crowned Merocyanine", *J. Phys. Chem.*, 1989, 3871-3876.

Descalzo, A. et al., "Coupling Selectivity with Sensitivity in an Integrated Chemosensor Framework: Design of a Hg2+-Responsive Probe, Operating above 500 nm", *J. Am. Chem. Soc.*, 2003, 3418-3419.
Fery-Forgues, S., "NMR and Optical Spectroscopy Studies of Cation Binding on Chromophores and Fluorophores Linked to Monoaza-15-Crown-5", *New .1. Chem.*, vol. 14, 1990, 617-623.
Iatridou, H et al., "The development of a new family of intracellular calcium probes", *Cell Calcium*, vol. 15, No. 2, Feb. 1994, 190-198.
Invitrogen, "Mp 01200: Fura and Indo Ratiometric Calcium Indicators", Product information sheet. Revised Jun. 21, 2005, Jun. 21, 2005, 1-6.
Invitrogen, "MP 06790: BTC Ion Indicators", *Molecular Probes Product Information Sheet*, http://probes.invitrogen.com/media/pis/mp06790.pdf, Jun. 20, 2005, 1-4.
Katerinopoulos, H. E., "The coumarin moiety as chromophore of flurescent ion indicators in biological systems.", *Current Pharmaceutical Design*, vol. 10, No. 30, 2004, 3835-3852.
Komatsu, Kensuke et al., "Development of an Iminocoumarin-Based Zinc Sensor Suitable for Ratiometric Fluorescence Imaging of Neuronal Zinc", *Journal of the American Chemical Society*, vol. 129, No. 44, 2007, 13447.
Levy, L.A et al., "Synthesis and Characterization of 19F NMR chelators for measurement of cytosolic free Ca", *American Journal of Physiology, Cell Physiology*, vol. 252, No. 4, 1987, 441-449.
Liepouri, F et al., "Iminocoumarin-based low affinity fluorescent Ca2+ indicators excited with visible light", *Cell Calcium*, vol. 30, No. 5, Nov. 2001, 331-335.
Liepouri, F. et al., "Near-membrane iminocoumarin-based low affinity fluorescent Ca2+ indicators", *Cell Calcium*, vol. 31, No. 5, May 2002, 221-227.
Morris, P.E, ""Synthesis of 5,5'difluoro-BAPTA-AM, a useful in vivo probe for calcium determination", Organic Preperations and Procedures International,", Aug. 1993, vol. 25, No. 4, pp. 445-448, 1993, 445-448.
Rurack, K. et al., "A Simple Bifunctional Fluoroionophore Signaling Different Metal Ions Either Independently or Cooperatively", *J. Am. Chem. Soc.*, 2001, 6205-6206.
Rurack, K. et al., "Cation-triggered 'switching on of the red/near infra-red (NIR) fluorescence of rigid fluorophore—spacer—receptor ionophores", *Chem Commun.*, 2000, 2103-2104.
Scheenen, Wim J. et al., "Intracellular Measurement of Calcium Using Fluorescent Probes", *Cell Blology: A Laboratory Handbook*, Second Edition, vol. 3, Academic Press (1998)., 1998, 363-374.
Smith, G. et al., "The Design and Properties of a Series of Calcium Indicators which Shift from Rhodamine-like to Fluorescein-like Flurescence on Binding Calcium", *J. Chem. Soc. Perkin Trans. 2*, 1993, 1195-1204.
Takahashi, Akiyuki, "Measurement of Intracellular Calcium", *Physiological Reviews*, vol. 79, Oct. 1999, 1089-1125.
Tsien, R. Y. et al., "A non-disruptive technique for loading calcium buffers and indicators into cells", *Nature*, vol. 290, No. 5806, Apr. 1981, 527-528.
Tsien, Roger Y. , "New Calcium Indicators and Buffers with High Selectivity against Magnesium and Protons: Design, Synthesis, and Properties of Prototype Structures", *Biochemistry*, 19, 1980, 2396-2404.

* cited by examiner

*Primary Examiner* — Kamal Saeed
(74) *Attorney, Agent, or Firm* — Life Technologies Corporation

(57) ABSTRACT

Disclosed are benzoxazole-based compounds, kits, and methods of producing and using the described compounds in fluorescence-based detection of analytes (e.g., metal ions). Also disclosed are uses of benzoxazole-based compounds as ratiometric metal ion indicators.

28 Claims, 8 Drawing Sheets

BENZOXAZOLE-BASED FLUORESCENT METAL ION INDICATORS

RELATED APPLICATIONS

This application is a U.S. National Stage Application of PCT Application No. PCT/US09/69696, filed Dec. 29, 2009, which claims priority to U.S. Provisional Application No. 61/141,181, filed Dec. 29, 2008, which disclosures are herein incorporated by reference in their entirety.

FIELD OF THE INVENTION

The present application relates to benzoxazole-based compounds; kits containing the described compounds; their use in the detection of metal ions (e.g., as ratiometric metal ion indicators).

BACKGROUND OF THE INVENTION

Fluorescent compounds are widely used in biological applications in which a highly sensitive detection reagent is desirable. In particular, the detection and quantification of calcium ion ($Ca^{2+}$) levels in biological systems has become an important area of investigation in biological and medical research. For example, the measurement of calcium ions inside live cells using fluorescent indicators provides realtime and end-point readout in a variety of biological investigative techniques and in high throughput screening (HTS) of drug candidates.

Numerous natural and synthetic materials are known to selectively or non-selectively bind to or chelate metal ions. Ion chelators are commonly used in solution for in vivo control of ionic concentrations and detoxification of excess metals, and as in vitro buffers. When bound to a fluorophore, ion chelators can often be used as optical indicators in metal ion analysis. Certain types of metal ion (e.g., $Ca^{2+}$) indicators utilize a chelating group in conjunction with a covalently attached fluorophore. One commonly used calcium ion chelating group is the tetracarboxylate chelating group based upon the structure of 1,2-bis-2-aminophenoxyethane-N,N,N',N'-tetraacetic acid (BAPTA). Upon formation of the BAPTA chelate, the fluorescence properties of the attached fluorophore is affected in some measurable way (e.g., emission is enhanced or decreased or the wavelength of excitation or emission is altered). $Ca^{2+}$ concentration can be determined using the measured fluorescence properties of a sample containing the indicator in conjunction with the dissociation constant for a specific indicator-$Ca^{2+}$ complex.

Certain types of fluorescence-based ion indicators respond to metal ion binding by changes in the fluorescence excitation and/or emission wavelength maxima. Indicators having such fluorescence properties can be used as ratiometric indicators. Ratiometric indicators are widely used in imaging applications and in flow cytometry to determine intracellular metal ion (e.g., $Ca^{2+}$) levels. Ratiometric measurements involve calculating a ratio between the excitation or emission intensity at two different wavelengths. Ratioing can reduce the effects of uneven dye loading, leakage of dye, photobleaching, and problems associated with measuring metal ions in cells of unequal thickness. Concentration measurements with ratiometric indicators generally are more convenient and accurate than measurements using intensity-based indicators.

Despite the abundance of fluorescent metal ion indicators (e.g., $Ca^{2+}$ indicators), known indicators suffer from various drawbacks. For example, many indicators have fluorescence properties in the ultraviolet region. UV excitable indicators require the use of specialized quartz optics and detection is complicated by interference from the environment (for example, due to the natural fluorescence many biological materials). Certain indicators exhibit an increase in emission intensity only upon binding to calcium ions. Indicators exhibiting only an emission intensity increase indicator frequently display no wavelength shift in either the excitation or emission spectrum upon binding, which makes it difficult to measure the concentration of metal ions, such as $Ca^{2+}$, using conventional ratiometric techniques. In addition, many ratiometric fluorescent metal ion indicators are limited to non-aqueous solutions due to insolubility or low quantum yield of the indicator in water or have metal ion binding affinities outside of physiologically relevant ranges. Despite continued research efforts, the assortment of the ratiometric fluorescent ion indicators available commercially is limited to two classes of calcium and magnesium indicators (Fura (excitation ratiometric), and Indo (emission-ratiometric) indicators). Examples of excitation ratiometric indicators include the sodium indicator SBFI and the potassium indicator PBFI. Members of the Fura and Indo classes of indicators can exhibit excitation ratiometry in the 300-335 nm region of the electromagnetic spectrum. However, the only available longer-wavelength excitation ratiometric calcium indicator, i.e. BTC, has a low calcium ion affinity ($K_d \sim 7000$ nM compared to ~200 nM for Indo and Fura), which limits its utility as a metal ion sensor.

Thus, there exists a need for fluorescent ratiometric indicators (in particular, emission ratiometric indicators) that are useful in the desirable visible wavelength range and are compatible with the aqueous systems commonly utilized in biological applications.

SUMMARY OF THE INVENTION

In one aspect, a novel class of metal ion indicators and methods of their preparation are provided. The metal ion indicators are fluorescent compounds that have a particularly high affinity for physiologically relevant metal ions. In one aspect, the metal ion indicator is compound of the following formula or a salt thereof:

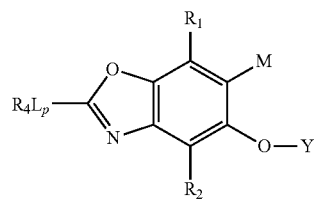

Wherein M is —$NCH_2$-Py or —$N(CH_2COOR_5)_2$, wherein $R_5$ is H, an alkyl having 1-6 carbons, —$CH_2OCOCH_3$, or a counterion. Y is —$CH_3$, —$CH_2COOH$, —$CH_2COOPy$, or

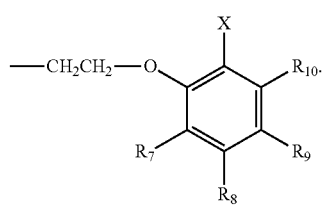

In certain embodiments, M is —N(CH$_2$COOH)$_2$ or —N(CH$_2$OCOCH$_3$)$_2$. X is —N(CH$_2$COOR$_5$)$_2$, —NCH$_2$Py, —OCH$_2$Py, or —OCH$_2$COOR$_5$. R$_7$, R$_8$, R$_9$, and R$_{10}$ can independently be alkyl having 1-6 carbons, halogen, amino, nitro, cyano, trifluoromethyl, sulfo, or sulfonamide. R$_1$ and R$_2$ are independently selected from the group consisting of H, an alkyl having 1-6 carbons, halogen, and sulfo. R$_4$ is a 5 or 6-membered aromatic ring or a fused ring system comprising at least one 6-membered aromatic ring. L is an alkylene having 2-6 carbons, and p is 0 or 1.

In another aspect, the metal ion indicator is compound of the following formula or a salt thereof:

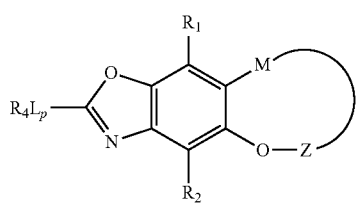

Wherein M is —NR$_3$—, wherein R$_3$ is —CH$_2$—Py, —CH$_2$Py, —CH$_2$CH$_2$OR$_5$, or —CH$_2$COOR$_5$, wherein R$_5$ is H, an alkyl having 1-6 carbons, —CH$_2$OCOCH$_3$, or a counterion. Z is

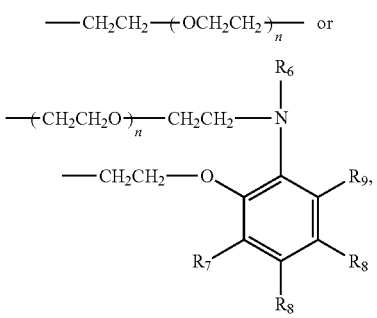

wherein n is 1, 2, or 3. R$_6$ is —CH$_2$COOR$_5$, —CH$_2$CH$_2$OR$_5$, —CH$_2$Py, or, when taken in combination with M, forms a structure

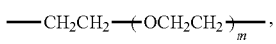

wherein m is 1, 2, or 3. R$_7$, R$_8$, R$_9$, and R$_{10}$ are independently selected from the group consisting of an alkyl having 1-6 carbons, halogen, amino, nitro, cyano, trifluoromethyl, sulfo, and sulfonamide. R$_1$ and R$_2$ are independently H, an alkyl having 1-6 carbons, halogen, or sulfo. R$_4$ is a 5 or 6-membered aromatic ring or a fused ring system comprising at least one 6-membered aromatic ring. L is an alkylene having 2-6 carbons, and p is 0 or 1.

Substituent R$_4$ can be substituted with an alkyl having 1-6 carbons, an alkoxy having 1-6 carbons, —OH, —COOH, COO$^-$, oxygen, halogen, —SO$_2$NH$_2$, or —N—R$_{10}$R$_{11}$, wherein R$_{10}$ and R$_{11}$ are independently H or an alkyl group having 1-6 carbon atoms. R$_{10}$ and R$_{11}$ can be independently, for example, methyl or ethyl. R$_4$ can include a heteroatom, such as O, N, and S, or can be phenyl or a substituted phenyl moiety.

Representative examples of R$_4$ include p-H$_2$NSO$_2$—C$_6$H$_4$—, p-KOOC—C$_6$H$_4$—, p-CH$_3$O—C$_6$H$_4$—, p-(CH$_3$)$_2$N—C$_6$H$_4$—,

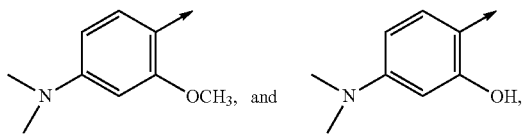

wherein K is H or a counterion.

Other examples of R$_4$ include

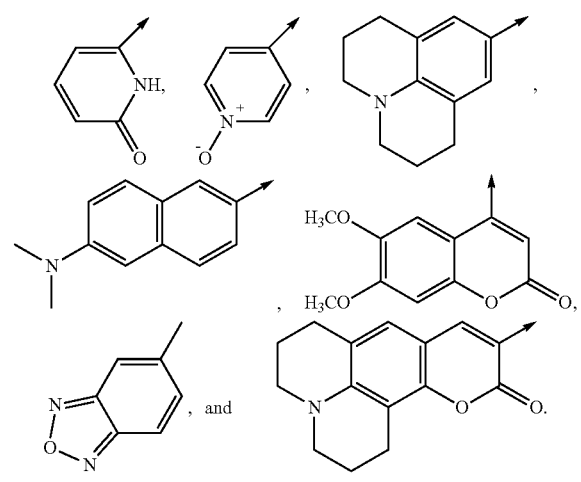

Yet another exemplary R$_4$ group is

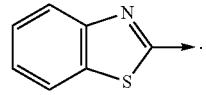

Yet other exemplary R$_4$ groups are Ph-CH=CH—, p-CH$_3$O—C$_6$H$_4$—

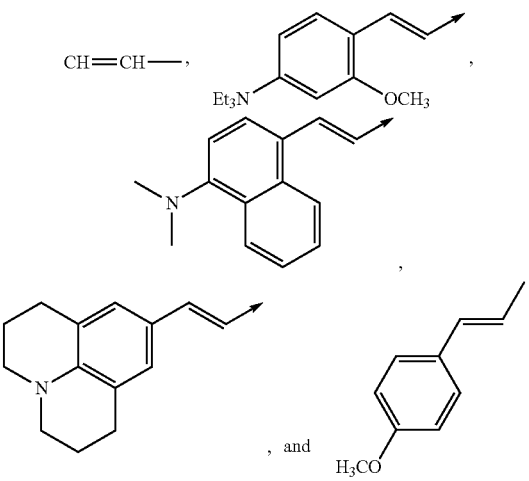

Yet other exemplary R₄ groups are Ph-CH=CH—, p-CH₃O—C₆H₄—CH=CH—, p-(CH₃)₂N—C₆H₄—CH=CH—, and

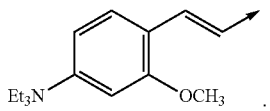

Yet other exemplary R₄ groups are

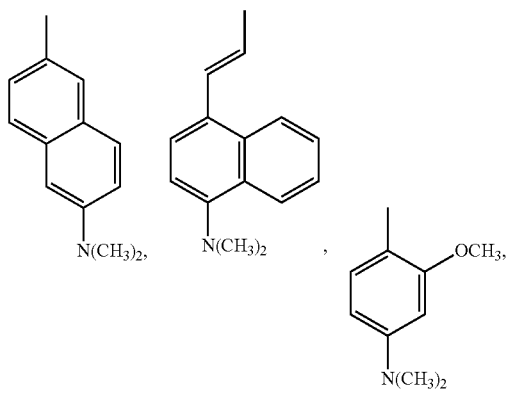

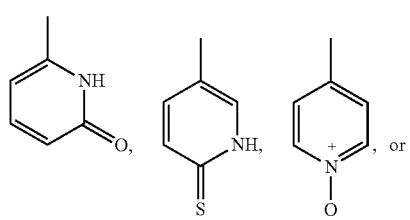

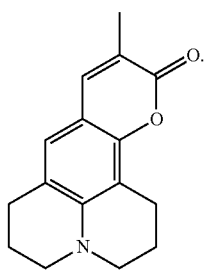

In yet another aspect, compounds of the following formulae or salts thereof are provided:

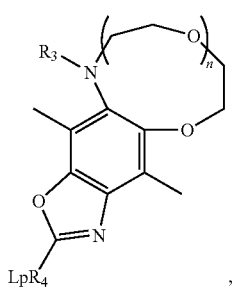

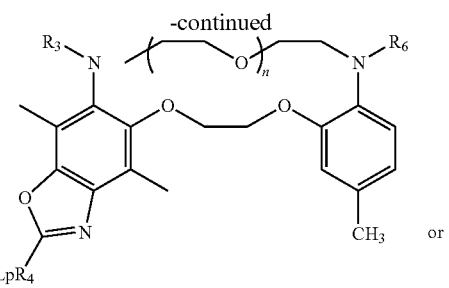

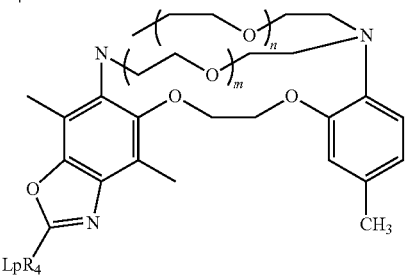

In yet another aspect, a compound of the following formula or a salt thereof is provided:

wherein M is —NCH₂-Py, —N(CH₂COOR₅)₂, wherein R₅ is H, an alkyl having 1-6 carbons, —CH₂OCOCH₃, or a counterion; X is —N(CH₂COOR₅)₂, —NCH₂Py, —OCH₂Py, or —OCH₂COOR₅; R₇, R₈, R₉, and R₁₀ are independently selected from the group consisting of an alkyl having 1-6 carbons, halogen, amino, nitro, cyano, trifluoromethyl, sulfo, and sulfonamide; R₁ and R₂ are independently H, an alkyl having 1-6 carbons, halogen, or sulfo; R₄ is a 5 or 6-membered aromatic ring or a fused ring system comprising at least one 6-membered aromatic ring; L is an alkylene having 2-6 carbons; and p is 0 or 1.

In yet another aspect, the disclosed compounds can further comprise a counterion, such as Na⁺, Li⁺, K⁺, Tl⁺, trialkylammonium and tetraalkylammonium.

In yet another aspect, the disclosed compounds can be in the form of an ester (e.g., AM ester) or a conjugate (e.g., a conjugate with a biomolecule (e.g., nucleic acid, oligonucleotide, polysaccharide).

In yet another aspect, the present compounds can form a complex with a metal ion, such as a polycationic metal ion. The polycationic metal ion can be, for example, a divalent metal ion, such as Ca²⁺, Zn²⁺, Mg²⁺, Pb²⁺, Hg²⁺, or Pb²⁺.

In yet another aspect, methods of using the described metal ion indicators for detection and quantification of metal ions in biological systems (e.g., as ratiometric metal ion indicators) are provided. An exemplary method of measuring the concentration of a polycationic metal ion (e.g., Ca²⁺) in a sample involves: a) combining a benzoxazole compound with a sample in an amount sufficient to generate a detectable fluorescent response to the metal ion; b) illuminating the sample to generate a fluorescence excitation or emission response; and c) observing the absorbance or emission response. A fluorometer, fluorescence microscope, laser scanner, flow cytometer can be used to observe the absorbance or emission response. The method can be used, for example, to examine samples that include living cells or biological fluids. The method can further include quantifying the fluorescence excitation or emission response. In certain embodiments, the compound exhibits a change in emission wavelength maximum upon binding to the polycationic metal ion. In other embodiments, the compound exhibits a change in excitation wavelength maximum upon binding to the polycationic metal ion.

In yet another aspect, kits containing the described metal ion indicators for use in detection and quantification of metal ions are provided. For example, a kit is provided for measuring the concentration of a polycationic metal ion in a sample that includes a benzoxazole compound, as described herein. The kit can further include one or more additional components, such as a salt solution having biological osmolarity, a buffer, and a metal ion solution.

These and other embodiments are described in further detail in the description and examples provided below.

DETAILED DESCRIPTION OF THE INVENTION

Figure 1A:
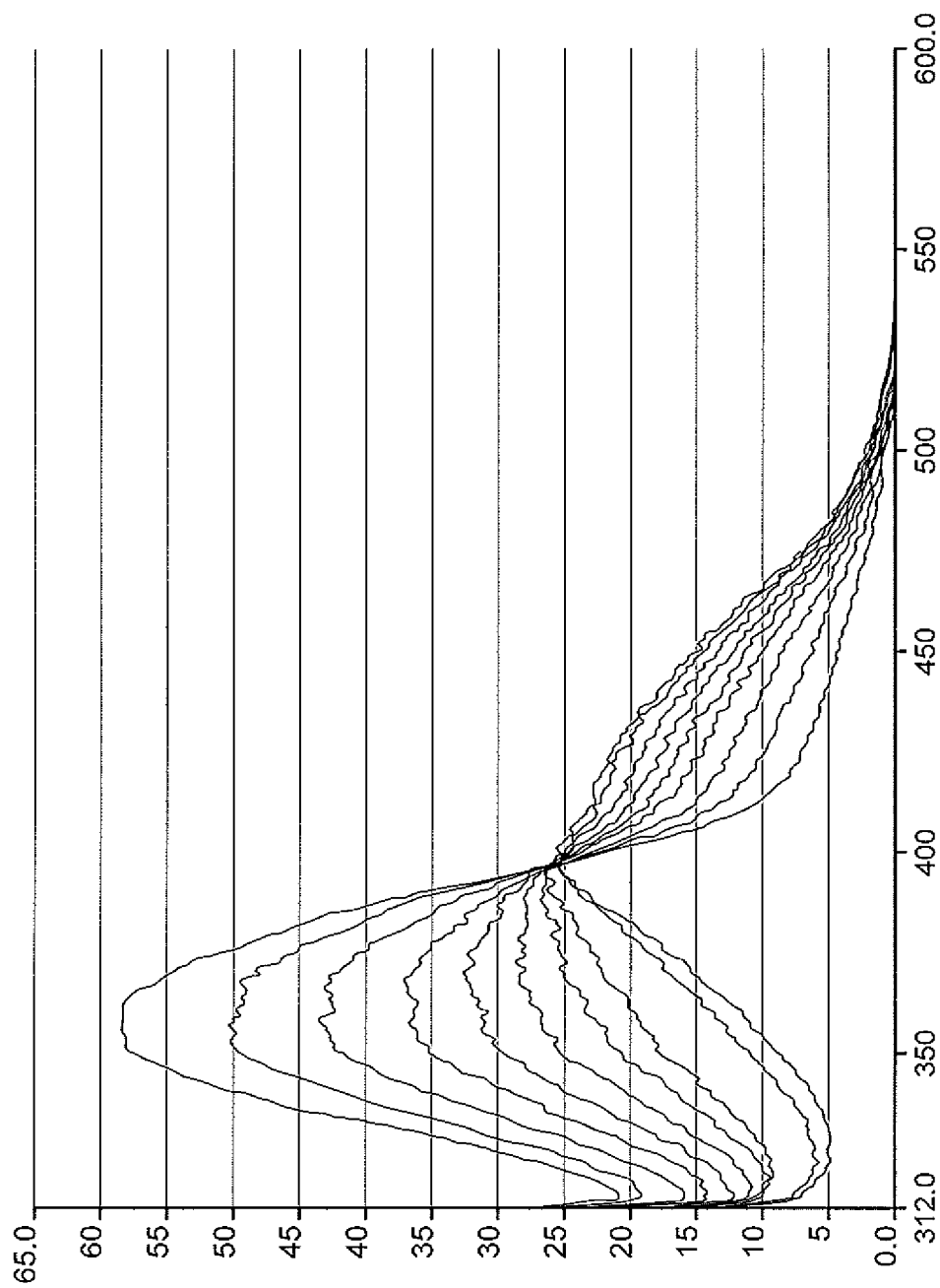
FIG. 1 is the excitation spectrum (A) (recorded at λemission=612 nm) and emission spectrum (B) (recorded at λexcitation=357 nm) of Compound 7k.

Before describing the present invention in detail, it is to be understood that this invention is not limited to specific compositions or process steps, as such may vary. It should be noted that, as used in this specification and the appended claims, the singular form "a", "an" and "the" include plural references unless the context clearly dictates otherwise. It also should be noted that the term "about", when used to describe a numerical value, shall encompass a range up to ±15% of that numerical value, unless the context clearly dictates otherwise.

Unless defined otherwise, all technical and scientific terms used herein have the same meaning as commonly understood by one of ordinary skill in the art to which this invention is related. The following terms are defined for purposes of the invention as described herein:

"Alkyl" refers to monovalent saturated aliphatic hydrocarbyl groups having from 1 to 10 carbon atoms and preferably 1 to 6 carbon atoms. This term includes, by way of example, linear and branched hydrocarbyl groups such as methyl ($CH_3$—), ethyl($CH_3CH_2$—), n-propyl($CH_3CH_2CH_2$—), iso-propyl(($CH_3$)$_2$CH—), n-butyl($CH_3CH_2CH_2CH_2$—), isobutyl(($CH_3$)$_2$CHCH$_2$—), sec-butyl (($CH_3$)($CH_3CH_2$)CH—), t-butyl(($CH_3$)$_3$C—), n-pentyl($CH_3CH_2CH_2CH_2CH_2$—), and neopentyl(($CH_3$)$_3$CCH$_2$—).

"Alkylene" refers to an alkyl chain.

"Alkoxy" refers to the group —O-alkyl wherein alkyl is defined herein. Alkoxy includes, by way of example, methoxy, ethoxy, n-propoxy, isopropoxy, n-butoxy, t-butoxy, sec-butoxy, and n-pentoxy.

"Aryl" or "Ar" refers to a monovalent aromatic carbocyclic group of from 5 to 14 carbon atoms having a single ring (e.g., benzo) or multiple condensed rings (e.g., naphthyl or anthryl) which condensed rings may or may not be aromatic.

"Amino" refers to the group —$NH_2$.

"H" indicates hydrogen.

"Halo" or "halogen" refers to fluoro, chloro, bromo and iodo.

"Hydroxy" or "hydroxyl" refers to the group —OH.

"Heteroaryl" refers to an aromatic group that contains at least one heteroatom selected from the group consisting of oxygen, nitrogen and sulfur within the ring. Such heteroaryl groups can have a single ring (e.g., pyridinyl or furyl) or multiple condensed rings (e.g., indolizinyl or benzothienyl) wherein the condensed rings may or may not be aromatic and/or contain a heteroatom.

"Heterocycle" or "heterocyclic" or "heterocycloalkyl" or "heterocyclyl" refers to a saturated or unsaturated group having a single ring or multiple condensed rings and at least one heteroatom selected from the group consisting of nitrogen, sulfur or oxygen within the ring wherein, in fused ring systems, one or more the rings can be cycloalkyl, aryl or heteroaryl.

"Salt" refers to pharmaceutically acceptable salts of a compound, which salts are derived from a variety of organic and inorganic counter ions well known in the art and include, by way of example only, sodium, potassium, calcium, magnesium, ammonium, and tetraalkylammonium; and when the molecule contains a basic functionality, salts of organic or inorganic acids, such as hydrochloride, hydrobromide, tartrate, mesylate, acetate, maleate, and oxalate.

"Sulfo" refers to sulfonic acid or a salt of sulfonic acid (sulfonate, $SO_3^-$).

The term "linker" or "L" refers to a covalent bond or a series of stable covalent bonds incorporating atoms selected from the group consisting of C, N, O, and S that covalently attach the fluorescent compounds to another chemical moiety. Exemplary linking members include a moiety that includes an alkylene group.

"Ratiometric fluorescence response" or "ratiometric response" refers to a change in a compound's fluorescence excitation and/or emission wavelength maxima upon binding to a metal ion. The response can be detected by monitoring the emission at a fixed wavelength. An excitation ratiometric response refers to a change in a compound's excitation wavelength maximum upon binding to a metal ion. An emission ratiometric response refers to a change in a compound's emission wavelength maximum upon binding to a metal ion while exciting at a fixed wavelength.

"Ratiometric measurement" refers to calculating a ratio between the excitation or emission intensity produced by a fluorescent compound at two different wavelengths.

Novel metal ion indicators are provided that exhibit a change in their fluorescence properties upon binding to metal ions The metal ion indicators have a particularly high affinity for physiologically relevant metal ions, such as calcium ($Ca^{2+}$). The measurement of the indicator's fluorescence can provide information on the metal concentration in a biological or non-biological sample. Certain compounds of the invention can function as ratiometric metal ion indicators (e.g., excitation or emission ratiometric indicators). The type of ratiometric response exhibited by a particular compound can be altered by varying particular substitutents on the oxazole moiety of the molecule.

In general, the compounds of the invention include a benzoxazole moiety substituted with a metal chelating moiety.

In one aspect, compounds are provided having a structure represented by Formula 1 or a salt thereof:

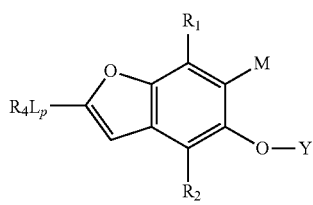

(Formula I)

Substituent M of Formula I can be any metal ion binding moiety. Representative examples of M include —$NCH_2$-Py (where Py is 2-pyridine) or —$N(CH_2COOR_5)_2$, wherein $R_5$ is H, an alkyl having 1-6 carbons, —$CH_2OCOCH_3$, or a counterion. $R_1$ and $R_2$ are independently H, an alkyl having 1-6 carbons, halogen, or sulfo. Substituent Y may be —$CH_3$, —$CH_2COOH$, or $CH_2COOPy$.

Substitutent Y has a structure represented by Formula 2:

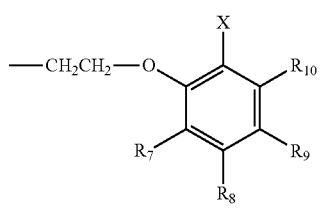

Formula 2

X may include any type of metal binding moiety, such as, for example, —$N(CH_2COOR_5)_2$, —$NCH_2Py$, —$OCH_2Py$, or —$OCH_2COOR_5$, where $R_5$ is as given above. Substituents $R_7$, $R_8$, $R_9$, and $R_{10}$, which may be the same or different, can be an alkyl having 1-6 carbons, a halogen, amino, nitro, cyano, trifluoromethyl, sulfo, or a sulfonamide.

Certain compounds of the invention include a 1,2-bis(o-aminophenoxy)ethane-N,N,N',N'-tetraacetic acid (BAPTA) chelator (Formula 3) or derivative thereof annelated to an oxazole moiety.

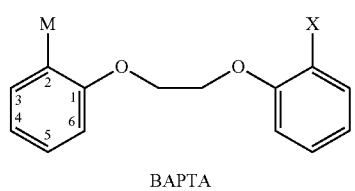

Formula 3

BAPTA

Compounds containing a BAPTA moiety may be depicted by the chemical structure of Formula 4, where the oxazole ring is substituted at the 2 position. The numbering of such compounds is based on Hantzsch-Widman nomenclature system considering BAPTA as substituted benzene ring.

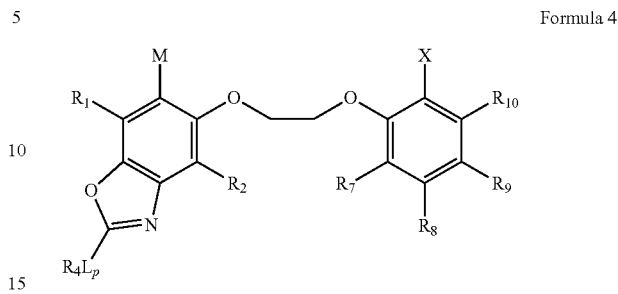

Formula 4

Compounds of Formula 4 may include any combination of substituents $R_1$, $R_2$, $R_7$, $R_8$, $R_9$, $R_{10}$, M, and X described herein. For certain compounds of the invention, however, both M and X are —$N(CH_2COOR_5)_2$, wherein $R_5$ is H or —$CH_2OCOCH_3$, or a counterion; $R_7$, $R_9$, and $R_{10}$ are H; and $R_8$ is alkyl (e.g., methyl or ethyl). In certain embodiments, compounds are provided that may be represented by the chemical structure of Formula 5.

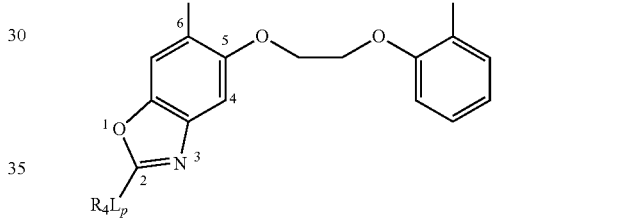

Formula 5

The oxazole ring of the subject compounds is substituted, either directly or via a linker, by a substitutent, $R_4$. In general, $R_4$ may be or include a 5 or 6-membered aromatic ring (e.g., phenyl) or a fused ring system comprising at least one 6-membered aromatic ring. The aromatic ring may be directly attached to linker, L, or to a carbon atom of the oxazole group (at the 2 position), such that p is 0 or 1 For p=0, $R_4$ is directed attached to a carbon atom of the oxazole moiety. When present (p=1), L may be, for example, an alkylene moiety having 2-6 carbon atoms. Depending on the nature of L and $R_4$, a particular compound may exhibit a change in the fluorescence excitation and/or emission wavelength maxima upon binding to a metal ion (i.e., ratiometric response). The type of ratiometric response exhibited may be altered by the varying the $R_4$ or L-$R_4$ substituents on the oxazole ring. For example, when $R_4$ (or a combination of L-$R_4$) is an electron-withdrawing group, or a moderately strong electron-donating group, an excitation-ratiometric response may be achieved. In contrast, when $R_4$ (or a combination of L-$R_4$) is an strong electron-donating group, an emission-ratiometric response may be achieved. Surprisingly, a change in oxazole substituent for a given core structure can produce a dramatic change in the compound's ratiometric response (e.g., from excitation-ratiometric to emission-ratiometric).

Representative examples of electron withdrawing groups that can yield a compound with an excitation ratiometric response include moieties such as cyano, carboxy, aldenyde, carbonyl, sulfo, nitrogen and oxygen heterocycles and the like. Moderate electron donating groups that can yield a compound with an emission ratiometric response include, for example, hydrogen atoms, hydroxyl groups, and alkoxy groups and the like. Strong electron donating groups that can yield a compound with an emission ratiometric response include, for example, substituted amino group, julolidine moiety and the like. Other types of electron withdrawing and donating groups may be used and are well known to the skilled artisan. In certain embodiments, benzoxazole compounds are provided that are substituted with strong electron donors, such as amino and julolidine moieities and exhibit an emission ratiometric response. An interesting outcome resulting from the attachment of the substituent through an olefinic double bond is that only the amplitude (and not the character) of the response changes.

In one embodiment, $R_4$ is a heteroaromatic ring that includes one or more oxygen, nitrogen, and/or sulfur atoms. $R_4$ may be unsubstituted or may be substituted with one or more substituents. As noted above, a unique feature of the subject metal ion indicators is that their fluorescence response can change from an excitation-ratiometric response to an emission-ratiometric response upon binding to metal ions. The tendency of a compound to exhibit an emission-ratiometric response depends, in particular, on the electron-donating or withdrawing ability of the aryl substituent of $R_4$.

In one embodiment, $R_4$ is a phenyl moiety, which may be unsubstituted or substituted. In other embodiments, $R_4$ is substituted with one or more groups selected from alkyl having 1-6 carbons, an alkoxy having 1-6 carbons, —OH, —COOH, COO⁻, oxygen, halogen, —SO$_2$NH$_2$, and —N—R$_{10}$R$_{11}$, wherein R$_{10}$ and R$_{11}$ are independently H or an alkyl group having 1-6 carbon atoms (e.g., methyl or ethyl).

Representative examples of $R_4$ include a substituted aryl or heteroaryl moiety, such as:

p-H$_2$NSO$_2$—C$_6$H$_4$—, p-KOOC—C$_6$H$_4$— (wherein K, wherein K is H or a counterion), p-H$_2$NSO$_2$—C$_6$H$_4$—, p-KOOC—C$_6$H$_4$—, p-CH$_3$O—C$_6$H$_4$—, and p-(CH$_3$)$_2$N—C$_6$H$_4$), p-CH$_3$O—C$_6$H$_4$—, and p-(CH$_3$)$_2$N—C$_6$H$_4$—.

Alternatively, $R_4$ may be a fused ring system that includes at least one 6-membered aromatic ring. The 6-membered aromatic ring may or may not be attached to the isoxazole moiety (or L, if present). Representative fused ring structures include those having two or more 5 or 6-membered aliphatic, aromatic, or heteroaromatic rings, where one or more of the rings in the fused ring structure may be substituted. Representative fused ring structures include:

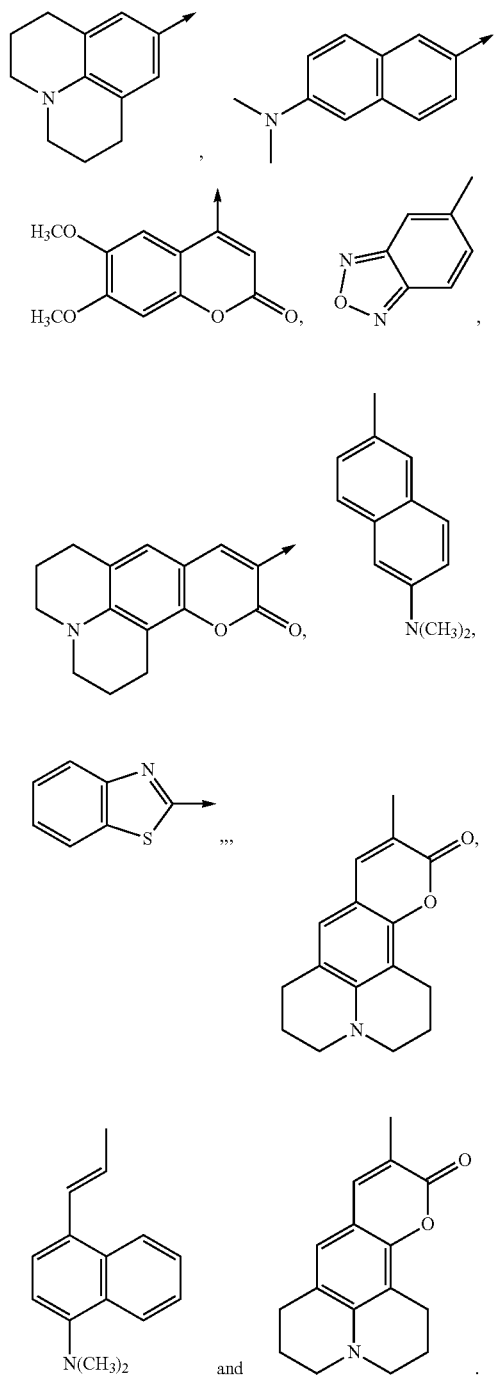

In certain embodiments, $R_4$ is bonded to the oxazole moiety via a linker, L. As noted above, L may be an alkylene moiety, such as an alkylene moiety having 2-6 carbons. In certain embodiments, $R_4$ is bonded to the oxazole moiety via an alkylene moiety having 2 carbons. Representative $R_4$ substituents that may be bonded to the oxazole system via an alkylene linker include the following:

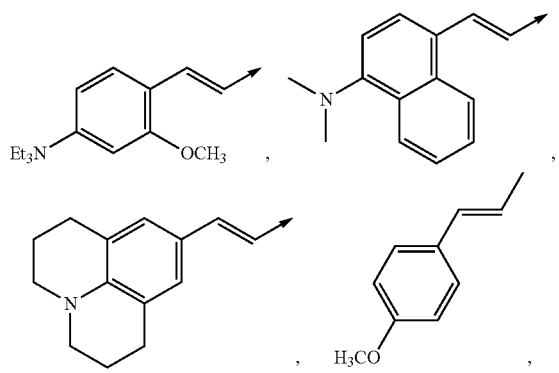

Ph—CH=CH—, and p-CH$_3$O—C$_6$H$_4$—CH=CH—, and —(CH$_3$)$_2$N—C$_6$H$_4$—CH=CH—. As noted above, introduction of an ethylene linker can reduce response amplitude (e.g., in Table I, compounds 7m-q containing ethylene linkers exhibit a less-pronounced response or have lost ratiometric properties altogether).

Also provided herein are compounds having a chemical structure represented by the Formula 6 or a salt thereof:

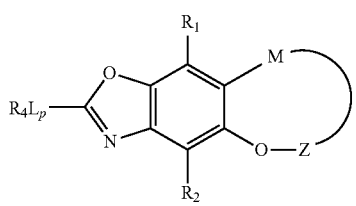

Formula 6

Substituents L, R$_1$, R$_2$, and R$_4$ of Formula 6 are as described above for Formula 1. Substituent M of Formula 6 is a metal binding moiety, such as NR$_3$—, wherein R$_3$ is —CH$_2$-Py, —CH$_2$Py, —CH$_2$CH$_2$OR$_5$, or —CH$_2$COOR$_5$, wherein R$_5$ is H, an alkyl having 1-6 carbons, —CH$_2$OCOCH$_3$, or a counterion. Substituent Z may be a polyalkylene oxide,

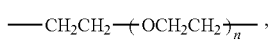

(where n=1, 2, or 3) or a substituted polyalkylene oxide having the structure represented in Formula 7:

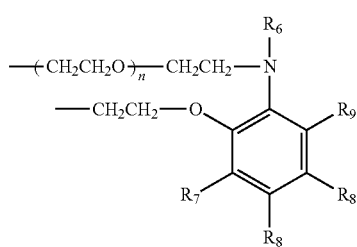

Formula 7

Substituent R$_6$ may be —CH$_2$COOR$_5$, —CH$_2$CH$_2$OR$_5$, —CH$_2$Py, or, when taken in combination with M, forms a polyalkylene oxide structure,

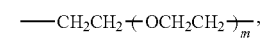

wherein m is 1, 2, or 3. Substituents R$_7$, R$_8$, R$_9$, and R$_{10}$ of Formula 7 are as described above in conjunction with Formula 2.

In certain embodiments, M and Z are connected via a polyalkylene oxide bridge to form a crown ether moiety. Representative examples of compounds comprising crown ether or cryptand moieties include the following:

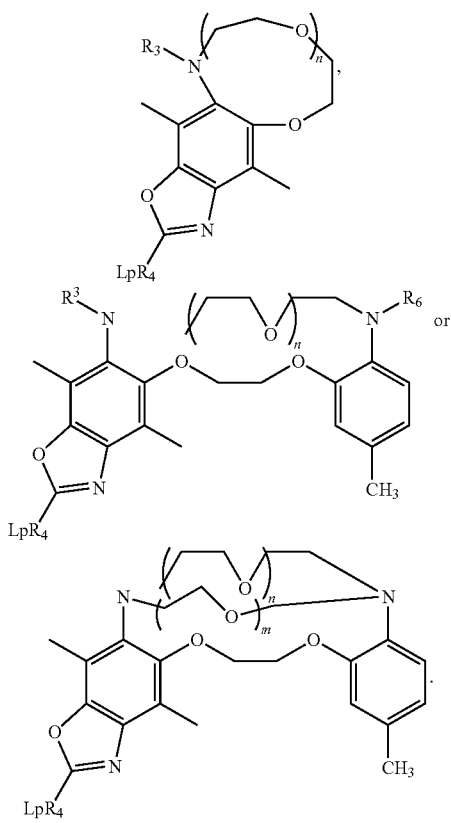

The compounds of the invention may be uncharged or may be in the form of a salt or ester. Salts of the described compounds are preferably non-toxic to living cells and do not interfere with the use of the compound as a metal ion indicator. Salts are typically carboxylic acid salts that may include a counterion such as, for example Na$^+$, Li$^+$, K$^+$, Tl$^+$, trialkylammonium or tetraalkylammonium. Typical esterifying groups include those that form hydrolysable esters, such as a-acyloxyalkyl esters (e.g., acetoxymethyl esters (CH$_3$CO$_2$CH$_2$—), and protect carboxylate groups. Esterification may be used to improve the solubility of the compound in non-aqueous (e.g., organic) solvents and/or allow the compound to more readily permeate cellular membranes. Once within the cell, intracellular enzyme (e.g., esterases) can hydrolyze the ester linkage to yield the deprotected compound (e.g., more polar acids and phenols) that are then well retained inside the cells.

Certain compounds can include a reactive moiety (e.g., activated ester, amine, azide, alkyne, and the like) that is capable of forming a conjugate with a compound, such as a biomolecule (e.g., protein, nucleic acid, oligonucleotide, oligosaccharide, dextran, and the like) or substrate (e.g., bead, particle, fiber, and the like). The biomolecule or substrate can be in its native state or derivatized to incorporate a reactive moiety that is capable of reaction with the reactive moiety of the benzoxazole compound.

The subject compounds are selective for metal ions. The metal binding moiety of the subject compounds are capable of binding (or chelating) to at least one metal ion to form a complex. The metal ion may be a metal ion that is monovalent or polyvalent (e.g., divalent or trivalent). In certain embodiments, the polyvalent metal ion is a divalent metal ion, such as $Ca^{2+}$, $Zn^{2+}$, $Mg^{2+}$, $Pb^{2+}$, $Hg^{2+}$, or $Pb^{2+}$. The disclosed compounds have particularly high binding affinities when contacted with $Ca^{2+}$. For example, typical calcium binding constants ($K_d$) of the disclosed compounds typically exceed about 100 nM; or about 150 nM; or about 200 nM; or about 250 nM; or about 300 nM. Compounds having calcium binding constants of about 100-300 nM can be used in many high throughput screening applications, whereas compounds having higher binding affinities (e.g., in the μM range) can be used for imaging neurons.

Particular benzoxazole-based fluorescent compounds absorb and emit light having a wavelength in the visible region of the electromagnetic spectrum (absorption: 300 to 500 nm; emission; 350 to 650 nm), although shorter or longer wavelengths of light may be used to excite these compounds, increasing the flexibility of their use. The ability to use light with longer wavelengths both for excitation and emission allows for the use of conventional optics and filters in conjunction with flow cytometry or fluorescence microscopy, for example), rather than the specialized and expensive quartz optics required for UV analysis needed for other types of metal ion indicators. Further, longer wavelength excitation and emission wavelengths allow the end user to avoid background associated with endogenous cellular fluorescence.

Methods of Preparing Benzoxazole Compounds

Also provided herein are methods of preparing the disclosed fluorescent compounds. A unique and unexpected feature of the indicators is that either excitation-ratiometric or emission-ratiometric indicators can be prepared using the same general method, with only minor variations in the chemical structure. The compounds may be prepared using known synthetic reactions, depending on the particular compound to be synthesized. By way of illustration, two synthetic routes (A and B in Scheme 1 below) are described for the preparation of compounds in which a benzoxazole ring is annelated with a BAPTA metal ion chelator. Both routes A and B use the same key intermediate, alpha-hydroxy nitroso compound 2, which is available through nitrosation of the 4-hydroxy BAPTA tetramethyl derivative 1, which is known in art [U.S. Pat. No. 5,454,517 (1995)]. Route A includes reduction of the nitroso group in intermediate 2 to form unstable amino derivative 3. This compound quickly decomposes while exposed to air, however it can be converted into benzoxazole derivative 6 upon heating with carboxylic acid 4 in polyphosphoric acid in oxygen-free conditions. The same benzoxazole derivative 6 can be made by route B in one step from key intermediate 2 by condensation with a halomethylene compound 6 in DMF at 100° C. in the presence of potassium carbonate as base. Methods A and B use different types of compounds (carboxylic acids 4 or halomethyl derivatives 5) to introduce substituent $R_4$ into the benzoxazole ring. Because the assortment of available carboxylic acids or halomethyl derivatives varies for different classes of compounds, use of complementary methods A or B is a way to prepare a wide range of benzoxazole derivatives 6.

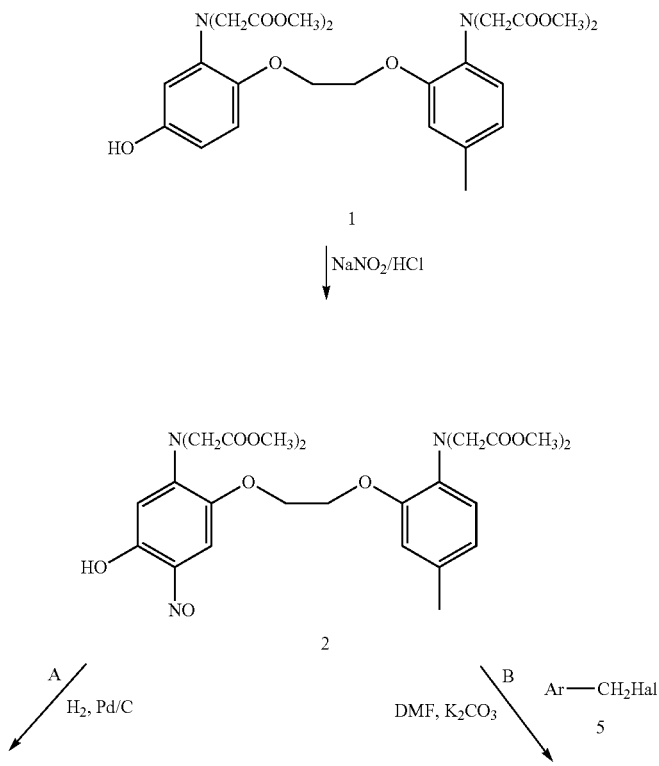

Scheme 1

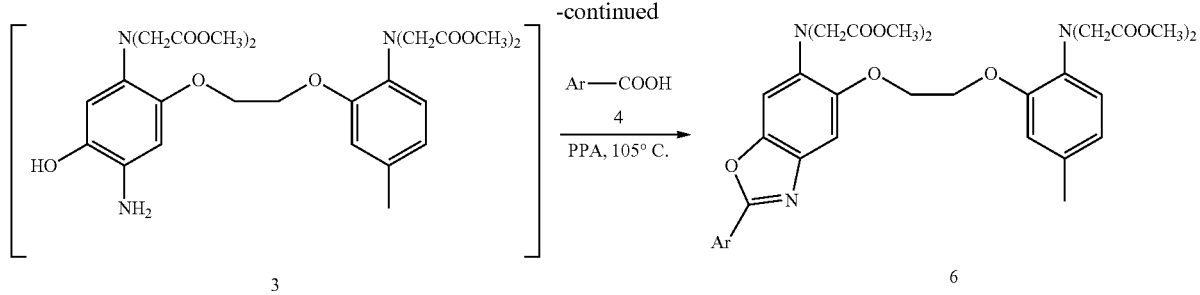

To prepare metal ion (e.g., Ca²⁺) indicators from the compounds 6, the four methyl groups protecting the BAPTA chelator are removed by treatment with KOH in water or with LiI in acetonitrile to give the tetracarboxylic salt 7 (Scheme 2). The later method allows deprotection of base-sensitive compounds, which otherwise can decompose upon treatment with potassium hydroxide in water. Compound 7 reacts with metal ions, such as Ca²⁺ ions, in aqueous solution to produce a fluorescent response, making these compounds useful as ion indicators in vitro or in extracellular applications. However, because the chelator moiety possesses four negative charges, these compounds cannot readily cross cellular membranes and are unable to be used in live cells without invasive permeabilization techniques such as microinjection, scrape loading, or electroporation. In order to make ion indicators passively cell-permeable, the carboxylic groups of compounds 7 may be protected with acetoxymethyl (AM) moieties according to method known in art (Tsien, R. Y. *Nature* 1981, 290, 527). The resulting AM tetraester 8 can be loaded readily into live cells by diffusion across the plasma membrane from the extracellular space into the cell interior. Upon entry into the cells, the four protective AM groups can be cleaved by cellular esterases to regenerate the indicator 7 in the anionic (metal-sensitive) form.

Applications and Methods of Use

The compounds provided herein may be used in various fluorescence-based assays to identify the presence and to quantitate the amount of metal ions in a sample. For example, such compounds may be added as part of a biological assay to measure the concentration of physiologically important metal ions, such as Ca²⁺, in intracellular and/or extracellular environments.

The compounds of the invention may be used to determine the presence of metal ions in a sample. Methods are provided to determine whether metal ions are present in a sample. Generally, the method involves a biologically compatible solution of the compound and then treating the sample (e.g., a biological material or cells) with the solution. After sufficient time for the compound to complex with metal ions in the sample, the sample is excited with a light source (e.g., a laser). Due to its optical properties, the compound can emit a fluorescence signal upon excitation. The subject compounds are capable of being excited by light and emit radiation in the visible region of the electromagnetic spectrum. The excitation range makes uses of commonly available excitation

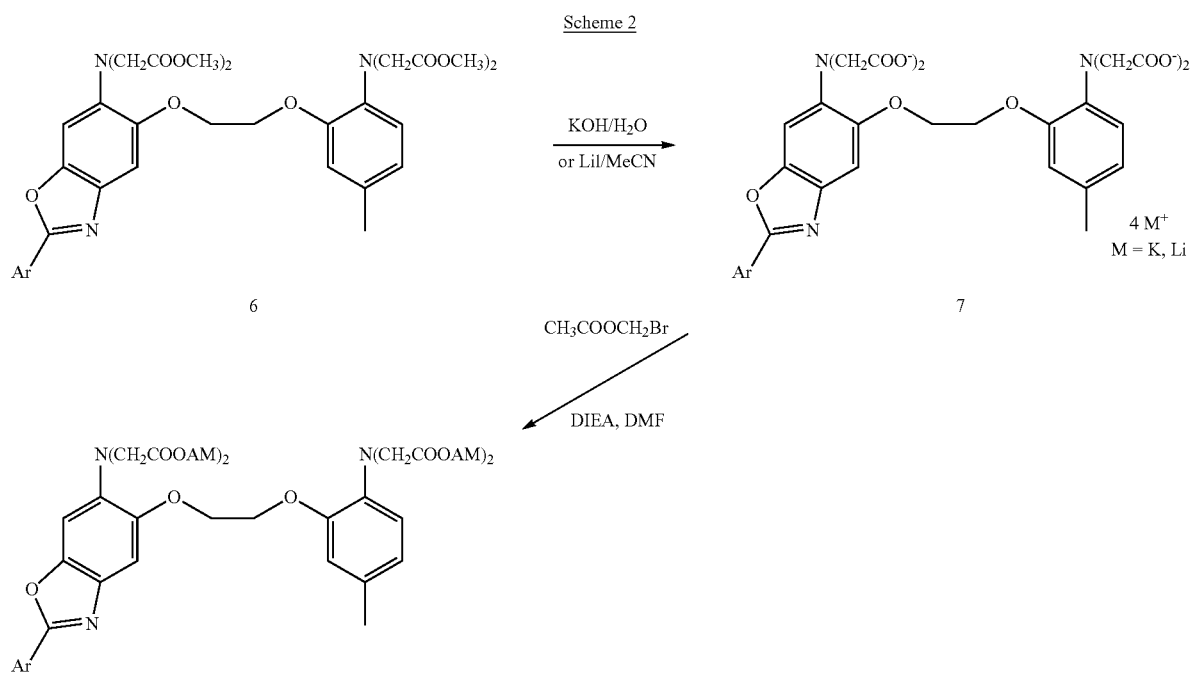

sources. Typically, the light source provides light having a wavelength that matches the absorption characteristics of the compound.

The subject compounds can exhibit a change in fluorescence properties upon binding the target metal ion, such as, for example, a divalent metal ion such as $Ca^{2+}$, $Zn^{2+}$, $Mg^{2+}$, $Pb^{2+}$, $Hg^{2+}$, or $Pb^{2+}$. Typically, the described compounds display a shift in excitation or emission maxima upon metal ion binding of greater than about ~20 nm. The measurement of the indicator's fluorescence spectrum can provide information on the concentration of metal ions in the sample. Particular compounds described herein exhibit a spectral shift upon binding to metal ions, which allows $Ca^{2+}$ detection or quantification by ratiometric analysis of the excitation or emission spectra of the indicator. A unique feature of the subject metal ion indicators is that the fluorescence response of the compound can change from an excitation-ratiometric response to an emission-ratiometric response simply be altering substituents on the oxazole moiety of the compound.

The compounds of the invention have longer excitation and emission wavelengths than many existing metal ion indicators (e.g., in the visible region of the electromagnetic spectrum) and are fully functional in aqueous solutions, making them compatible with biological systems and assays. The long wavelength excitation and emission bands of particular compounds enables their use with a variety of optical devices and require no specialized (quartz) optics, such as are required by indicators which are excited or emit at shorter wavelengths. Accordingly, these indicators are suitable for use in fluorescence microscopy, flow cytometry, fluoroscopy, or any other application that currently utilize fluorescent metal ion indicators.

Methods of using the disclosed compounds for detection (and, optionally, quantitating) metal ions in a sample are provided. The compounds may be used to detect the presence of various types of metal ions and are particularly sensitive for the detection of polycationic metal ion such as $Ca^{2+}$. An exemplary method for measuring the concentration of a polycationic metal ion in a sample involves combining a compound of the invention with a sample in an amount sufficient to generate a detectable fluorescent response to the metal ion. The sample is then illuminated to generate a fluorescence excitation or emission response, and the absorbance or emission response is detected. The methods provided herein may further include quantification of the fluorescence excitation or emission response. Certain compounds, for example, may exhibits a change in emission wavelength maximum upon binding to the polycationic metal ion, whereas other types of compounds may exhibit a change in excitation wavelength maximum upon binding to the polycationic metal ion.

Samples may be of biological or non-biological origin. Certain types of samples contain living cells or biological fluids. The indicator is combined with a sample in a way that will facilitate detection of the target ion concentration in the sample. The sample is generally a fluid or liquid suspension that is known or suspected to contain the target ion. Representative samples include intracellular fluids such as in blood cells, cultured cells, muscle tissue, neurons and the like; extracellular fluids in areas immediately outside of cells; in vesicles; in vascular tissue of plants and animals; in biological fluids such as urine, cerebrospinal fluid, blood, lymph fluids, tissue homogenate, interstitial fluid, cell extracts, mucus, saliva, sputum, stool, physiological secretions or other similar fluids; in biological fermentation media; in environmental samples such as water, soil, waste water and sea water; and in chemical reactors.

Compounds disclosed herein are useful for of detecting and quantifying metal cation levels in living cells, biological fluids or aqueous solutions. Typically, the sample is obtained directly from a liquid source or as a wash from a solid material (organic or inorganic) or a growth medium in which cells have been introduced for culturing, or a buffer solution in which cells have been placed for evaluation. Where the sample comprises cells, the cells are optionally single cells, including microorganisms, or multiple cells associated with other cells in two or three dimensional layers, including multicellular organisms, embryos, tissues, biofilms, and the like. The sample may also come from any solid tissue, which is disaggregated to allow for a suspension of single cells to be labeled and tested on a flow cytometer.

The compounds are advantageously used to identify the presence of metal ions in samples with biological components. The sample may comprise heterogeneous mixtures of components (including intact cells, cell extracts, bacteria, viruses, organelles, and mixtures thereof), or a single component or homogeneous group of components (e.g. natural or synthetic amino acid, nucleic acid or carbohydrate polymers, or lipid membrane complexes). The described compounds are generally non-toxic to living cells and other biological components, within the concentrations of use.

The present compounds generally are utilized by combining the compound with a sample of interest under conditions selected to yield a detectable optical response. The compound typically associates in a non-covalent manner to form a complex with a metal ion or ions in the sample, or is simply present within the bounds of the sample or portion of the sample. The sample is then illuminated at a wavelength selected to elicit the optical response.

A detectable optical response means a change in, or occurrence of, an optical signal that is detectable over the concentration range of interest either by observation or instrumentally. Typically the detectable response is a change in fluorescence, such as a change in the intensity, excitation or emission wavelength distribution or maxima of fluorescence, fluorescence lifetime, fluorescence polarization, or a combination thereof.

For biological applications, the compounds of the invention are typically used in an aqueous, mostly aqueous or aqueous-miscible solution prepared according to methods generally known in the art. The compounds of the invention are typically soluble in biologically compatible solvents, such as water, buffer, media, media with additions like serum or antibiotics, DMSO, DMF, or the like, which allows for easy sample preparation for fluorescence-based assays. The exact concentration of compound is dependent upon the experimental conditions and the desired results. The indicator concentration is dictated by the dissociation constant of the ion-indicator complex and may be determined according to techniques that are well known in the art. The optimal amount of compound is determined empirically with each cell type, buffer or media, cell concentration, testing procedure and testing platform used and is determined by systematic variation until satisfactory results with minimal background fluorescence are accomplished, but typically in the micromolar range.

The compound is combined with the sample in any way that facilitates contact between the compound and the sample components of interest. Typically, the compound or a solution containing the compound is simply added to the sample. For example, the indicator may be dissolved in solution at a concentration that is optimal for detection of the indicator at the expected concentration of the target ion. Certain compounds of the invention tend to be permeant to membranes of biological cells, and once inside viable cells are typically well retained. Modifications that are designed to enhance permeability of the indicator through the membranes of living cells, such as acetoxymethyl esters and acetates, may require the indicator to be predissolved in an organic solvent such as dimethylsulfoxide (DMSO) before addition to a cell suspension.

The ability of the present compounds to rapidly and effectively enter living cells facilitates their use in assays to probe living cells Treatments that permeabilize the plasma membrane, such as detergents or alcohols, such as electroporation, shock treatments or high extracellular ATP can be used to introduce selected compounds into cells. Alternatively, selected compounds can be physically inserted into cells, e.g. by pressure microinjection, scrape loading, patch clamp methods, or phagocytosis.

Equipment that is useful for illuminating the dye compounds of the invention includes, but is not limited to, hand-held ultraviolet lamps, mercury arc lamps, xenon lamps, lasers and laser diodes. These illumination sources are optionally integrated into flow cytometers, fluorometers, fluorescence microscopes, laser scanners, fluorescence microplate readers, and the like.

The optical response is optionally detected by visual inspection, or by use of any of the following devices: CCD cameras, video cameras, photographic film, laser-scanning devices, fluorometers, photodiodes, quantum counters, epifluorescence microscopes, scanning microscopes, flow cytometers, fluorescence microplate readers, or by means for amplifying the signal such as photomultiplier tubes. Where the sample is examined using a flow cytometer, examination of the sample for data analysis, or for sorting portions of the sample according to their fluorescence response.

As discussed above, the described compounds have an affinity for metal ions (e.g., divalent ions) and can form a complex with metal ions, which can be detected optically. The complex may be formed with a compound that is uncharged or in a salt form or a combination of forms. The complex may be formed by association of one or more metal ions with a compound of the invention. In certain embodiments, the complex is formed when a compound, as described herein, associates with calcium ions ($Ca^{2+}$). In other embodiments, the compound selectively binds to monovalent alkali cations (e.g., $Li^+$, $Na^+$, $K^+$, and the like) or heavy metal ions (e.g., ($Cd^{2+}$, $Hg^{2+}$, $Pb^{2+}$, and the like).

The complex may be present in a biological sample wherein the biological sample includes cells, or the isolated nuclei of cells. The cells may be live or dead cells. In certain embodiments, the biological sample includes live cells. The compounds provided herein have application for both fixed specimens and viable cells.

Methods for detection of metal ions in a sample may further include quantitating the metal ions detected. Quantification of metal ion levels in samples is accomplished using the present indicators by ratiometric methods known in the art. The ratiometric method provides accurate measurement of ion concentrations by the treatment of the fluorescence data as the ratio of excitation or fluorescence intensities at two wavelengths, rather than the absolute intensity at a single wavelength. Using the ratio method, a number of variables that may perturb the ion concentration measurements are eliminated. In particular, ion-dependent factors that affect the signal intensity, such as non-uniform intracellular dye concentrations, probe leakage, dye bleaching and cell thickness, are canceled in the ratio measurements, since these parameters have a similar effect on intensities at both wavelengths. While the ratio method can be used to determine concentrations using observation of either the excitation spectra of the indicator, the emission spectra of the indicator, or both, in the case of the described indicators, the shift in excitation energy upon binding metal ions makes observation of the excitation spectrum a more useful technique. In either case, the indicator should be calibrated (to compensate for variance in the dissociation constant of the indicator due to ionic strength, viscosity, or other conditions within the cell). To calibrate the indicator, ionophores such as ionomycin are used. Non-ratiometric analysis can also be accomplished by calibration with a second fluorescent compound present in the sample.

In one aspect, methods of quantifying metal ion content in live cells are provided. Eukaryotic cells in a resting state maintain an internal calcium ion concentration below that of the external environment. Ionized calcium plays an important role in transmembrane signal transduction. Increases in the intracellular calcium ion concentration help to regulate a diverse range of cellular processes in living cells, making measurement of intracellular calcium ion concentration and changes in concentration valuable. A flow cytometer can be used to measure the concentrations of various intracellular free ions in living cells, among these are calcium ions. Flow cytometry can be used to measure intracellular calcium ion concentration in large numbers of cells, and can correlate ion concentration with other parameters, such as immunophenotyping and DNA content, in a multiplexing fashion.

In certain embodiments, a ratiometric-indicator dye is loaded into a cell. In certain embodiments, the cell has low levels of $Ca^{2+}$. The ratiometric indicator emits fluorescence in a particular wavelength range. As calcium enters the cytoplasm, it can bind to the indicator, causing a spectral shift (e.g., a shift in absorption or emission wavelength). A ratio measurement between the two fluorescence responses can be measured, for example, using a flow cytometer. In addition, an instrument capable of cell sorting can sort cells based on the calcium response, with the sorted cells cultured for later analysis. Ratio-generated signals generally are independent of cell size or brightness and can change in proportion to the change in calcium levels over time. The use of a ratio measurement also eliminates the need to perform the complex calibrations required by other non-ratiometric methods. Ratiometric measurement can cancel out extraneous factors, such as the effect of cell-to-cell variations in indicator loading. Further, ratiometric measurement can be used to discriminate responses of small subpopulations of cells.

In another aspect, the compounds of the invention are incorporated into kits that facilitate the detection of metal ions. The kits can be packaged with the compound in a dry form or with the compound in solution. The kits may optionally further include one or more buffering agents, typically present as an aqueous solution, sample preparation reagents, additional detection reagents, organic solvent, other fluorescent detection probes, standards, microspheres, specific cell lines, antibodies or instructions for carrying out an assay. Additional optional agents include other components for testing of other cell functions in conjunction with the compound. In certain embodiments, kits are provided that include a compound of the invention and a salt solution having biological osmolarity, a buffer, and/or a metal ion solution.

The following examples are given for the purpose of illustrating the invention and shall not be construed as being a limitation on the scope of the invention or claims.

EXAMPLES

Compounds can be synthesized using the methods described in the following examples or by other methods, which are known in the art. It should be understood that the organic compounds may exhibit the phenomenon of tautomerism. As the chemical structures within this specification can only represent one of the possible tautomeric forms, it should be understood that any tautomeric form is encompassed by the drawn structure.

Example 1

Synthesis of the 4-hydroxy-5-nitroso-BAPTA tetramethyl ester (Compound 2)

To a stirred solution of 4-hydroxy derivative (Compound 1) (4.40 g, 7.9 mmol) in 1:1 aqueous HCl (200 mL) a solution of $NaNO_2$ (0.65 g, 9.4 mmol) in 3 mL $H_2O$ was introduced under the surface over 5 mL upon cooling to 3-5° C. The reaction mixture was stirred for 1 h at 5° C. and was poured into 3N NaOAc (1.2 L). The foamy precipitate was allowed to coagulate upon standing for 2 h, filtered off, washed with water to neutral pH, and dried in vacuum dessicator to give compound 2 as brown solid; yield 3.62 (78%). Compound 2 was pure by NMR and used without additional purification.

Example 2

Synthesis of the 2-R-BAPTO[d]oxazole tetramethyl ester (Compound 6) from carboxylic acid (Compound 4) (Route A)

A general procedure is described for the preparation of 2-R-BAPTO[d]oxazole tetramethyl ester (Compound 6) from carboxylic acid (Compound 4) via Route A. Nitroso derivative (Compound 2) (0.591 g, 1 mmol) was hydrogenated at atmospheric pressure over 0.100 g 10% Pd/C catalyst in $CHCl_3$ (20 mL) for 2 h. The mixture was filtered under argon from catalyst and evaporated without access to air. To the solid residue the acid (Compound 4) (1.5 mmol), polyphosphoric acid (~2 g) and dioxane (2 mL) were added and the mixture was placed into a pre-heated 100° C. bath and stirred for 4 h under argon. The resulting syrup was cooled to rt and treated with 50 mL $CHCl_3$ and 50 mL $H_2O$. Organic layer was separated and the aqueous phase was extracted with $CHCl_3$ (5×20 mL). Combined organic portions were washed with sat. $NaHCO_3$ (3×150 mL), sat. NaCl (150 ml), dried over $MgSO_4$ and evaporated. The crude product was purified by column chromatography on silica gel using $CHCl_3$ as eluant to give the tetramethyl ester (Compound 6) in 5% to 50% yield.

Example 3

Synthesis of the 2-R-BAPTO[d]oxazole tetramethyl ester (Compound 6) from halomethyl derivative (Compound 5) (Route B)

A general procedure is described for the preparation of 2-R-BAPTO[d]oxazole tetramethyl ester (Compound 6) from halomethyl derivative (Compound 5) viat Route B. A mixture of nitroso compound (Compound 2) (0.295 g, 0.5 mmol), halomethyl derivative (Compound 5) (0.6 mmol), potassium carbonate (0.345 g, 2.5 mmol), and NaI (0.045 g, 0.3 mmol, catalytic) in DMF (5 ml) was stirred for 3 h at 100° C. Upon cooling to rt it was poured into $H_2O$ (200 mL) and extracted with $CHCl_3$ (10×50 mL). The organic extract was washed with $H_2O$ (3×200 mL), sat. NaCl (200 mL), dried over $MgSO_4$, and evaporated. The crude product was purified by column chromatography on silica gel using $CHCl_3$ as eluant to give the tetramethyl ester (Compound 6) in 5% to 30% yield.

Example 4

General Procedure for Deprotection of the 2-R-BAPTO[d]oxazole tetramethyl ester (Compound 6) with potassium hydroxide A solution of tetramethyl ester (Compound 6) (0.02 mmol) in dioxane (1 mL) and methanol (1 mL) was treated with 1N KOH (0.3 mL, 0.3 mmol) and stirred for 16 h. The mixture was diluted with water, and the pH lowered to ~9 with 0.2N HCl, and evaporated. The residue was dissolved in water, loaded onto a Sephadex LH-20 column (1.5×50 cm bed, packed and equilibrated with water) and chromatographed using $H_2O$ as eluant. The fractions containing product were combined together, evaporated to 2 mL volume and lyophilized to obtain product (Compound 7) as fine flakes in 50-80% yield.

Example 5

General Procedure for Deprotection of the 2-R-BAPTO[d]oxazole tetramethyl ester (Compound 6) with lithium iodide A mixture of tetramethyl ester (Compound 6) (0.05 mmol) and Li—I (0.670 g, 5 mmol) in MeCN (5 ml) was refluxed under stirring for 24 h. After cooling to rt it was diluted with acetone (5 ml), allowed to stand for 1 h, and the crude product was filtered off, washed with cold acetone (5 mL) and ether (2×5 mL). The lithium salt was dissolved in water, loaded onto SEPHADEX LH-20 column (2.5×100 cm bed, packed and equilibrated with water) and chromatographed using $H_2O$ as eluant. The fractions containing product were combined together, evaporated to 2 mL volume and lyophilized to get the product (Compound 7) as fine flakes in 50-70% yield. The described procedure can be used to prepare various BAPTA derivatives, such as 7a, 7m, or 7q.

Example 6

General Procedure for Preparation of the 2-R-BAPTO[d]oxazole tetra(acetoxymethyl) ester (Compound 8)

A solution of tetracarboxylic acid salt (Compound 7) (0.1 mmol) in water was acidified to pH 3.0 with aqueous HCl. The precipitated acid was quickly filtered off and dried in high vacuum for 2 h. It was dissolved in DMF (3 mL) and DIEA (0.25 mL, 2 mmol) and bromomethyl acetate (0.14 mL, 1.5 mmol) were added. The mixture was stirred for 16 h, diluted with $CHCl_3$ (50 mL) and washed with 1% AcOH (3×50 mL), water (50 mL) and sat. NaCl (50 ml). It was filtered from water droplets and evaporated. The crude product was purified by column chromatography on silica gel using $CHCl_3$ as eluant to give the tetra(acetoxymethyl) ester (Compound 8) in 70% to 80% yield.

Example 7

Spectrofluorimetry Studies

The excitation and emission spectra of solutions of various ion indicators (concentration 1-2 µM) were recorded in 30 mM MOPS and 100 mM KCl buffers containing 0 to 200 nM free calcium ion. The binding constant values were calculated based on 8-10 data points taken in buffers covering the concentration range appropriate for the Kd value. Spectral curves for derivatives of Compound 7 (with different R substitutents) were recorded using a standard spectrofluorimeter.

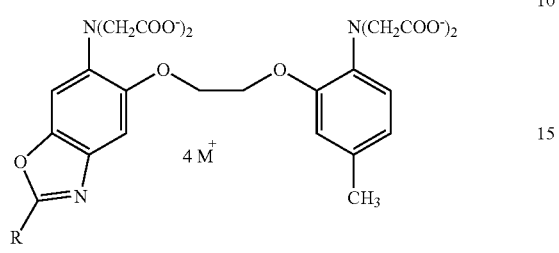

Compound 7

Figure 1B:
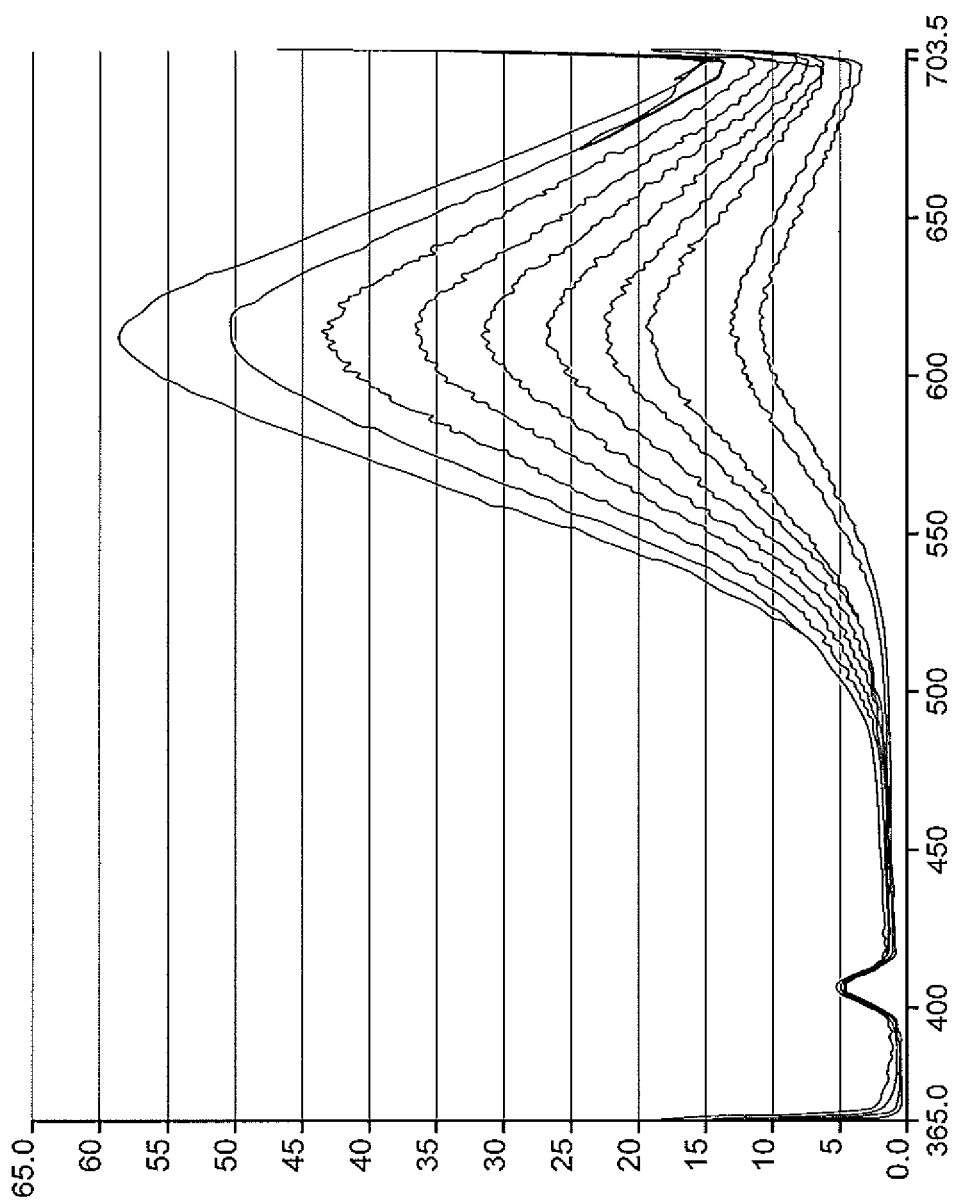
Figure 2A:
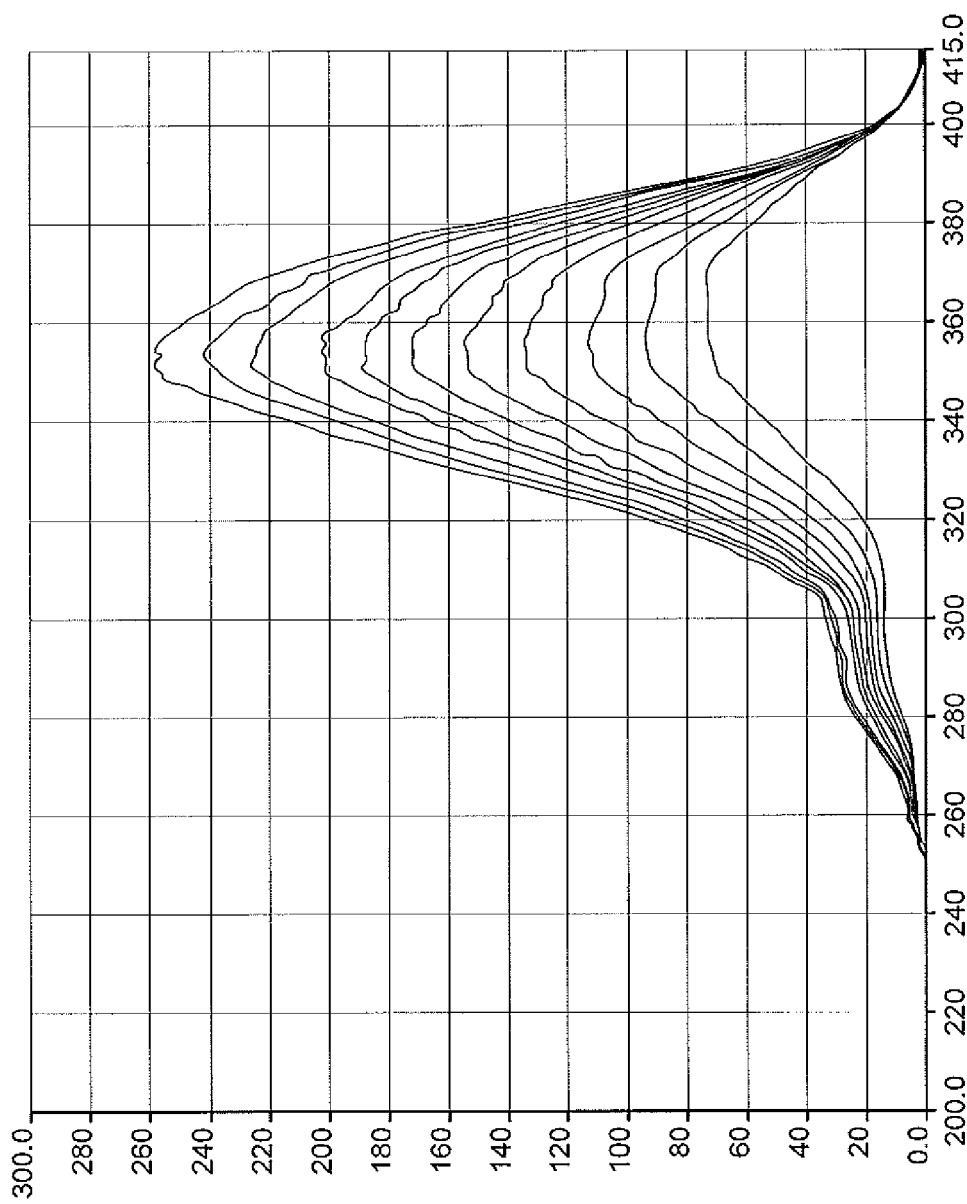
FIG. 2 is the excitation spectrum (A) (recorded at λemission=425 nm) and emission spectrum (B) (recorded at λexcitation=363 nm) of Compound 7e.
Figure 2B:
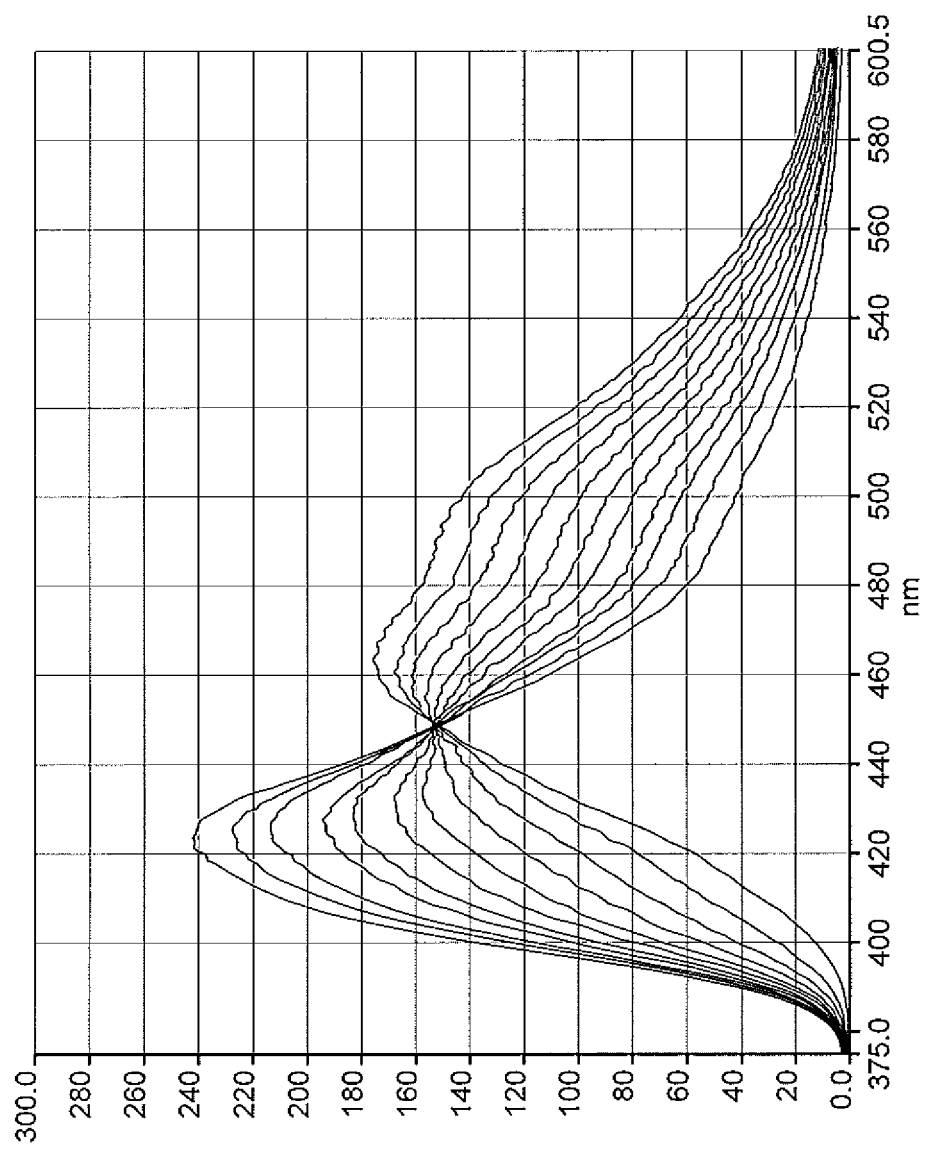
Figure 3A:
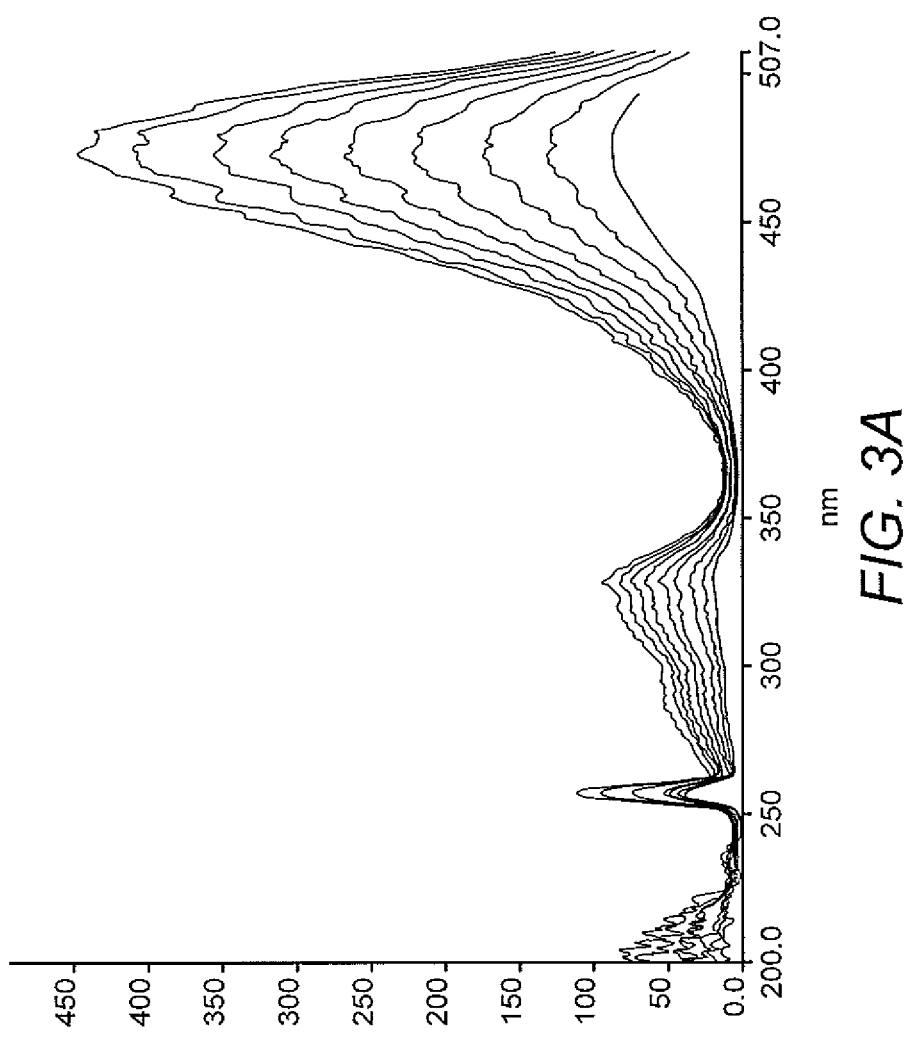
FIG. 3 is the excitation spectrum (A) (recorded at λemission=520 nm) and emission spectrum (B) (recorded at λexcitation=472 nm) of Compound 7t.
Figure 3B:
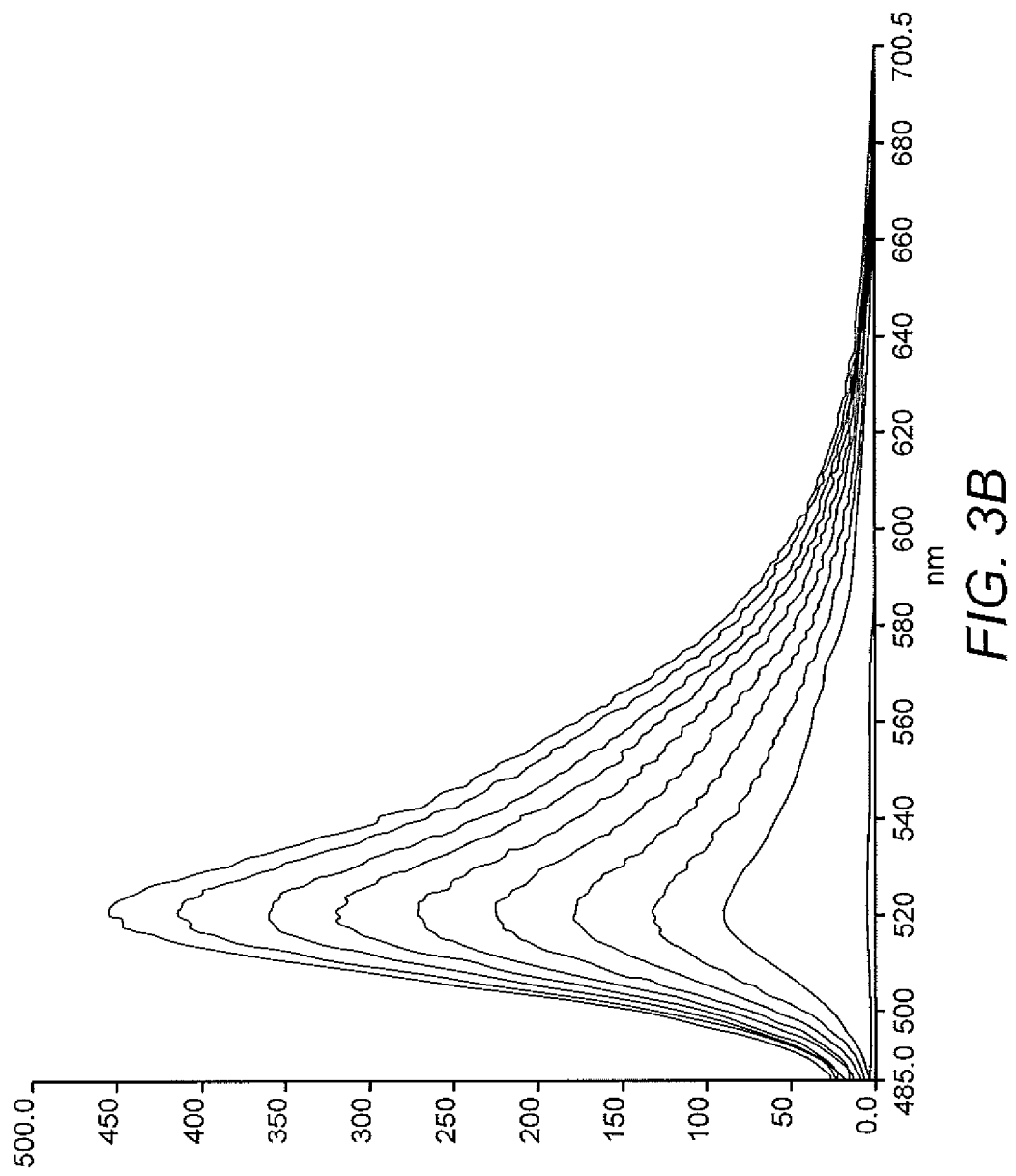

FIGS. 1-3 show excitation and emission spectra for several of the tested compounds. Referring to FIG. 1, the spectral curves of the Compound 7k exemplify an excitation-ratiometric response to metal ion binding (FIG. 1), while spectral curves of Compound 7e exemplify an emission-ratiometric response to binding (FIG. 2). Spectral curves of Compound 7t exemplify a non-ratiometric response to metal ion binding (FIG. 3). Table 1 provides spectral and ion binding characteristics for compounds of the invention (Table 2).

TABLE 1

Spectral and Ion-Binding Characteristics for Compound 7 Derivatives

| Compound | $\lambda_{abs}$ (UV), (nm) | $\lambda_{excit}$ (nm)[a] | $\lambda_{emiss}$ (nm)[a] | $K_d(Ca^{2+})$ (nM) | Ratiometric Response |
|---|---|---|---|---|---|
| 7a | 322 | 330-365 | 488 | 123 | excitation |
| 7b | 297 | 295-320 | 385 | 158 | excitation |
| 7c | 358 | 340-380 | 358 | 162 | excitation |
| 7d | 350 | 338-365 | 475 | 141 | excitation |
| 7e | 363 | 363 | 416-475 | 101 | emission |
| 7f | 363 | 363 | 417-475 | 103 | emission |
| 7g | 363 | 363 | 417-496 | 85 | emission |
| 7h | 375 | 375 | 435-510 | 145 | emission |
| 7i | 364 | 361-422 | 569 | 309 | excitation |
| 7j | 366 | 349-392 | 567 | 146 | excitation |
| 7k | 357 | 356-425 | 612 | 304 | excitation |
| 7l | 330 440 (non-emissive) | 324-364 | 490 | 157 | excitaton |
| 7m | 373 | 348-420 | 550 | 164 | excitation |
| 7n | 268 | 300-380 | 540 | 144 | excitation |
| 7o | 415 | 417 | 527-570 | 187 | emission[b] |
| 7p | 392 | 392 | 586 | 290 | non-ratiometric |
| 7q | 413 | 413 | 548 | 80 | non-ratiometric |
| 7r | 373 | 373 | 496 | 129 | non-ratiometric |
| 7s | 364 | 364 | 550 | 222 | non-ratiometric |
| 7t | 472 | 472 | 520 | 156 | non-ratiometric |

[a]The position of maxima for two ratiometric peaks
[b]The ratiometric response is not well-pronounced

TABLE 2

Compound 7 Derivatives

| Compound | R = |
|---|---|
| 7a | $C_6H_5-$ |
| 7b | $p-H_2NSO_2-C_6H_4-$ |
| 7c | $p-KOOC-C_6H_4-$ |
| 7d | $p-CH_3O-C_6H_4-$ |
| 7e | $p-(CH_3)_2N-C_6H_4-$ |
| 7f | (3-dimethylamino-6-methoxyphenyl) |
| 7g | (3-dimethylamino-6-hydroxyphenyl) |
| 7h | (julolidinyl) |
| 7i | (benzothiazol-2-yl) |
| 7j | (6-oxo-1,6-dihydropyridin-2-yl) |
| 7k | (pyridinyl N-oxide) |
| 7l | (benzofurazanyl) |
| 7m | $Ph-CH=CH-$ |
| 7n | $p-CH_3O-C_6H_4-CH=CH-$ |
| 7o | $(Et_2N, OCH_3\text{-styryl})$ |

TABLE 2-continued

Compound 7 Derivatives

| Compound | R = |
|---|---|
| 7p | (structure) |
| 7q | (structure) |
| 7r | (structure) |
| 7s | (structure) |
| 7t | (structure) |

Example 8

Flow Cytometry Studies

Figure 4A:
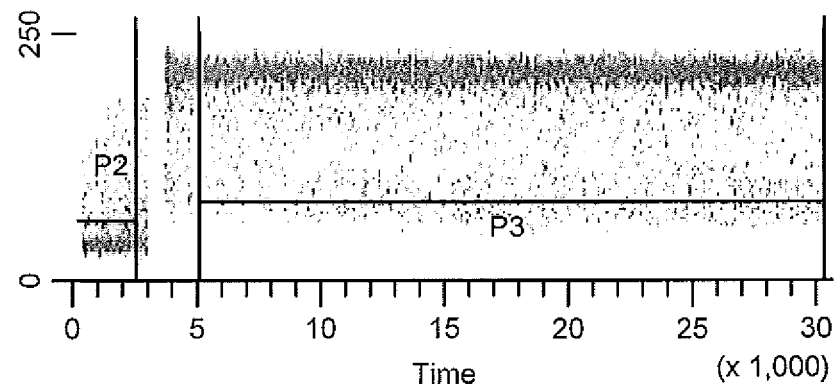
FIG. 4 is a dual parameter showing intracellular calcium response for cells loaded with Compound 7e, upon addition of ionomycin (A) or CD3 (B).
Figure 4B:
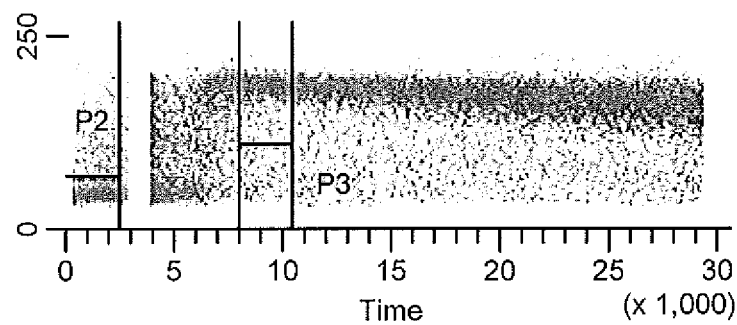
Figure 5A:
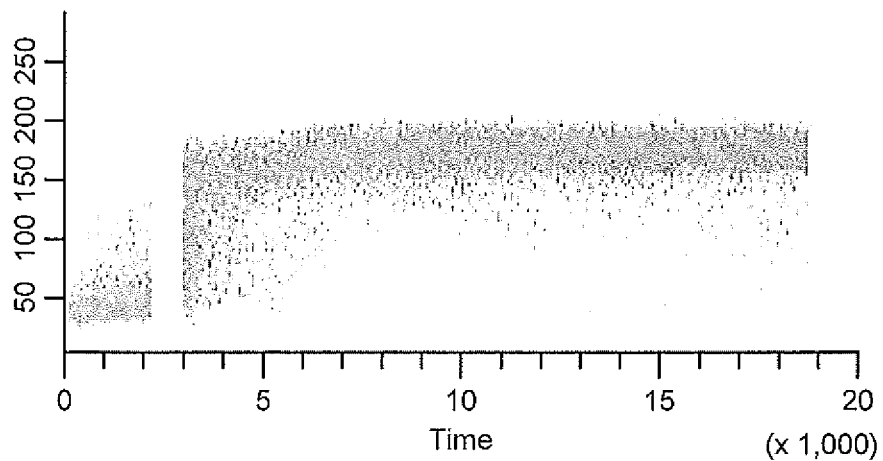
FIG. 5 is a dual parameter showing intracellular calcium response for cells loaded with Compound 7f, upon addition ionomycin (A) or CD3 (B).
Figure 5B:
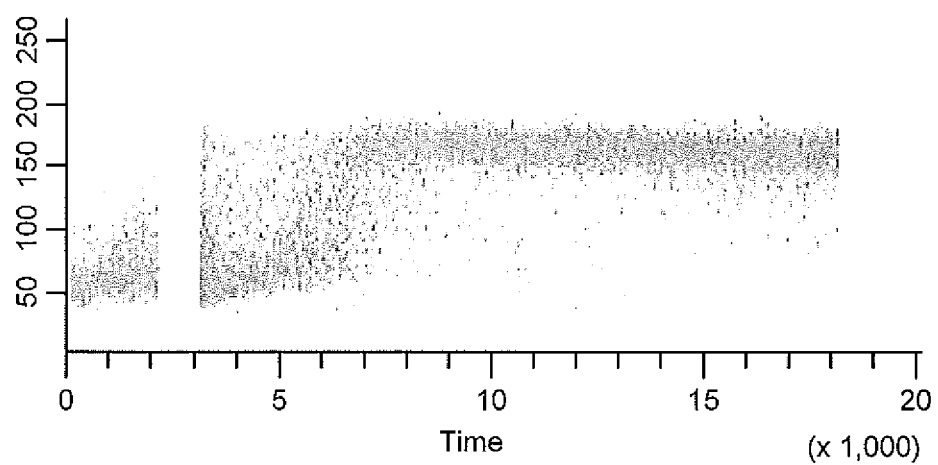

Jurkat T-cell leukemia cultured cells were washed once with Hanks Buffered Salt Solution (HBSS) containing calcium and resuspended in HBSS at a concentration of $2 \times 10^6$/ml. A one (1) mL cell suspension was added to a 12×75 mm test tube. A cell-permeant compound (7e or 7f) was added to the cell suspension at a final concentration of 4 μM. The cell/dye mixture was mixed and placed at 37° C. protected from light for 30 minutes. The sample then was washed once with HBSS pre-warmed to 37° C. and the cell pellet was resuspended in one mL warmed HBSS. The sample rested for 15 minutes at 37° C. protected from light. A Becton Dickinson (BD) LSRII flow cytometer equipped with 355 nm and 488 nm lasers were used for data acquisition and analysis using DIVA software. The sample was run through the LSRII instrument, and the main cell population was gated to eliminate debris using the 488 nm laser light scatter parameters. On the gated cells, measurements using 355 nm excitation and a ratio measurement of emission collected in bandpass filters of 495/20 and 424/44 were used. The sample was placed on the instrument and data collection was started to establish a baseline. The sample was removed from the instrument without stopping collection of data, and either control or a stimulant such as ionomycin or CD3 was added to the sample. The sample then was mixed and replaced on the instrument with data acquisition continuing. Analysis of the data was performed using a dual parameter plot of time versus fluorescence ratio of the emissions as measured by 495/20:424/44 ratio. When DMSO was added to the sample, it served as a control and did not cause a change in calcium concentration above baseline. When 1 μM final concentration ionomycin was added, an immediate intracellular calcium response of all cells was seen, which was maintained over time. When CD3 was added, an immediate intracellular calcium response of cells was seen, with the response decreasing slightly over time. The results of the assay using Compound 7e and Compound 7f are shown in FIG. 4 and FIG. 5, respectively. A plot of time versus fluorescence ratio for cells that have been loaded with the tested compound was collected upon addition of ionomycin or CD3 stimulant after baseline measurement. A marker (P2) was placed on the baseline response and another marker (P3) was placed on the response after addition of stimulant. For Compound 7e, the ratio of the mean fluorescence as measured yielded an increase of 3.4× with ionomycin stimulation (A), an expected response which was maintained over time. The ratio of the mean fluorescence as measured gave an increase of 2.8× with CD3 stimulation (B), an expected response which decreased slightly over time. For Compound 7f, the ratio of the mean fluorescence gave an increase of 3.2× with ionomycin stimulation (A), an expected response which is maintained over time, and the ratio of the mean fluorescence as measured gives an increase of 2.8× with CD3 stimulation, an expected response which decreases slightly over time (B).

All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A compound of the formula:

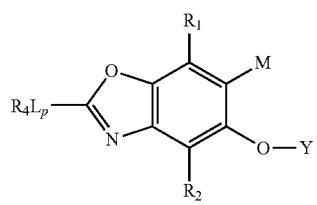

or a salt thereof,
wherein M is —NCH$_2$-Py or —N(CH$_2$COOR$_5$)$_2$, wherein R$_5$ is H, an alkyl having 1-6 carbons, —CH$_2$OCOCH$_3$, or a counterion;
Y is —CH$_3$, —CH$_2$COOH, —CH$_2$COOPy, or

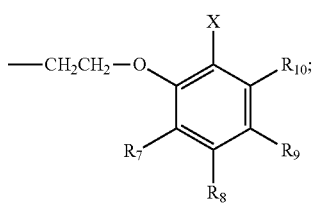

X is —N(CH₂COOR₅)₂, —NCH₂Py, —OCH₂Py, or —OCH₂COOR₅;

R₇, R₈, R₉, and R₁₀ are independently selected from the group consisting of an alkyl having 1-6 carbons, halogen, amino, nitro, cyano, trifluoromethyl, sulfo, and sulfonamide;

R₁ and R₂ are independently H, an alkyl having 1-6 carbons, halogen, or sulfo;

R₄ is a 5 or 6-membered aromatic ring or a fused ring system comprising at least one 6-membered aromatic ring;

L is an alkylene having 2-6 carbons; and p is 0 or 1.

2. A compound of the formula:

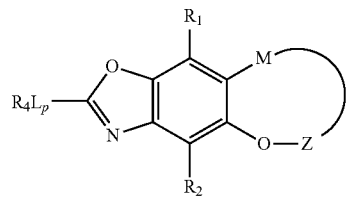

or a salt thereof, wherein M is —NR₃—, wherein R₃ is —CH₂-Py, —CH₂Py, —CH₂CH₂OR₅, or —CH₂COOR₅, wherein R₅ is H, an alkyl having 1-6 carbons, —CH₂OCOCH₃, or a counterion;

Z is

—CH₂CH₂—(OCH₂CH₂)ₙ— or

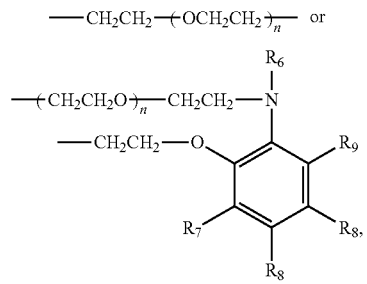

wherein n is 1, 2, or 3;

R₆ is —CH₂COOR₆, —CH₂CH₂OR₅, —CH₂Py, or, when taken in combination with M, forms a structure

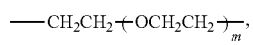

wherein m is 1, 2, or 3;

R₇, R₈, R₉, and R₁₀ are independently selected from the group consisting of an alkyl having 1-6 carbons, halogen, amino, nitro, cyano, trifluoromethyl, sulfo, and sulfonamide;

R₁ and R₂ are independently H, an alkyl having 1-6 carbons, halogen, or sulfo;

R₄ is a 5 or 6-membered aromatic ring or a fused ring system comprising at least one 6-membered aromatic ring;

L is an alkylene having 2-6 carbons; and p is 0 or 1.

3. The compound of claim 1 or 2 wherein R₄ is substituted with an alkyl having 1-6 carbons, an alkoxy having 1-6 carbons, —OH, —COOH, COO⁻, oxygen, halogen, —SO₂NH₂, or —N—R₁₀R₁₁, wherein R₁₀ and R₁₁ are independently H or an alkyl group having 1-6 carbon atoms.

4. The compound of claim 1 or 2 wherein R₁₀ and R₁₁ are independently methyl or ethyl.

5. The compound of claim 1 or 2 wherein R₄ comprises a heteroatom selected from O, N, and S.

6. The compound of claim 1 or 2 wherein R₄ is phenyl or a substituted phenyl moiety.

7. The compound of claim 1 or 2 wherein R₄ is selected from p-H₂NSO₂—C₆H₄—, p-KOOC—C₆H₄—, p-CH₃O—C₆H₄—, p-(CH₃)₂N—C₆H₄—,

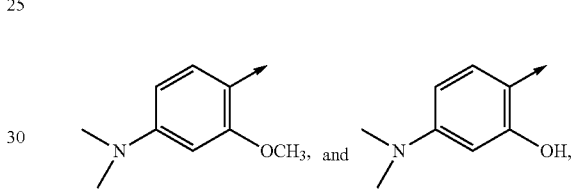

wherein K is H or a counterion.

8. The compound of claim 1 or 2 wherein R₄ is selected from the group consisting of

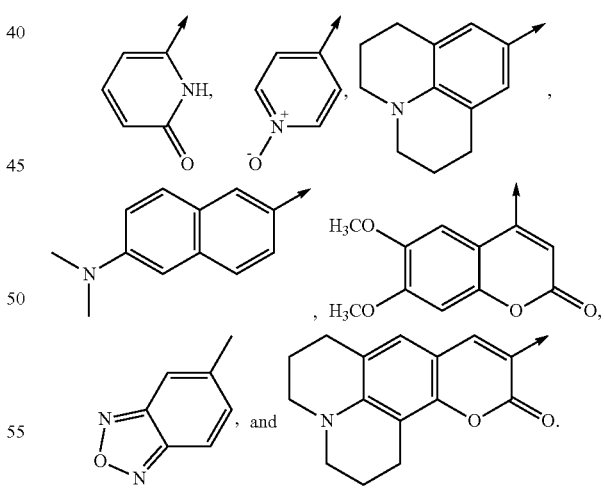

9. The compound of claim 1 or 2 wherein R₄ is

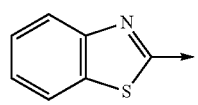

10. The compound of claim 1 or 2 wherein $R_4$ is selected from Ph—CH=CH—, p-CH$_3$O—C$_6$H$_4$—CH=CH—,

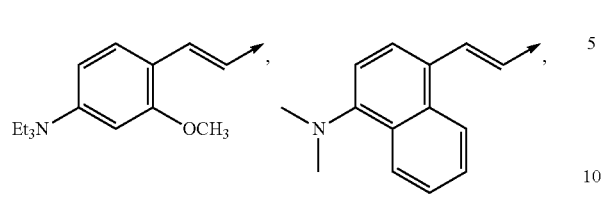

11. The compound of claim 1 or 2 wherein $R_4$ is selected from Ph—CH=CH—, p-CH$_3$O—C$_6$H$_4$—CH=CH—, p-(CH$_3$)$_2$N—C$_6$H$_4$—CH=CH—, and

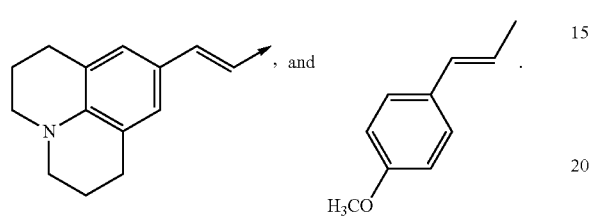

12. The compound of claim 1 or 2 wherein $R_4$ is

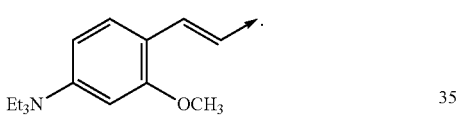

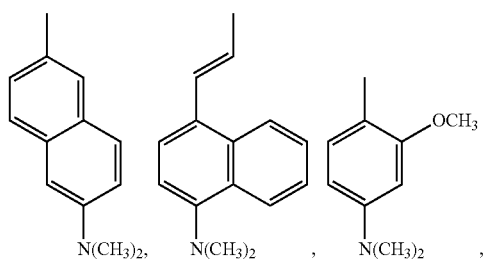

13. The compound of claim 1 or 2 wherein M is —N(CH$_2$COOH)$_2$ or —N(CH$_2$OCOCH$_3$)$_2$.

14. The compound of claim 2 having the formula

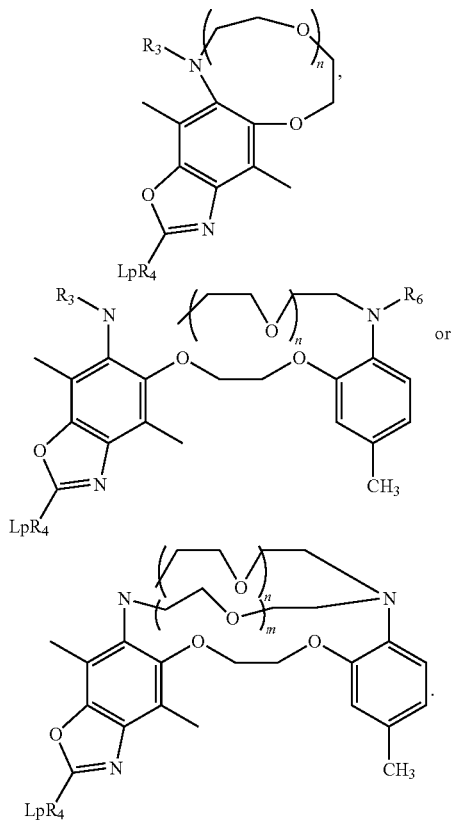

15. A compound of the formula

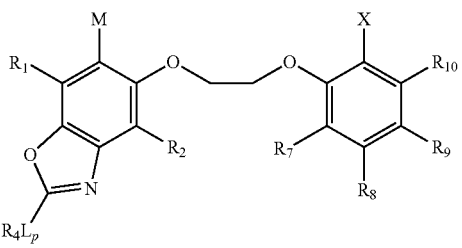

or a salt thereof,
wherein M is —NCH$_2$-Py, —N(CH$_2$COOR$_5$)$_2$, wherein $R_5$ is H, an alkyl having 1-6 carbons, —CH$_2$OCOCH$_3$, or a counterion;

X is —N(CH$_2$COOR$_5$)$_2$, —NCH$_2$Py, —OCH$_2$Py, or —OCH$_2$COOR$_5$;

$R_7$, $R_8$, $R_9$, and $R_{10}$ are independently selected from the group consisting of an alkyl having 1-6 carbons, halogen, amino, nitro, cyano, trifluoromethyl, sulfo, and sulfonamide;

$R_1$ and $R_2$ are independently H, an alkyl having 1-6 carbons, halogen, or sulfo;

$R_4$ is a 5 or 6-membered aromatic ring or a fused ring system comprising at least one 6-membered aromatic ring;

L is an alkylene having 2-6 carbons; and p is 0 or 1.

16. The compound of claim 1 or 2, further comprising a counterion selected from $Na^+$, $Li^+$, $K^+$, $Tl^+$, trialkylammonium and tetraalkylammonium.

17. A complex comprising a compound of claim 1 or 2 and a polycationic metal ion.

18. The complex of claim 17 wherein the polycationic metal ion is a divalent metal ion.

19. The complex of claim 17 wherein the polycationic metal ion is $Ca^{2+}$, $Zn^{2+}$, $Mg^{2+}$, $Pb^{2+}$, $Hg^{2+}$, or $Pb^{2+}$.

20. A method of measuring the concentration of a polycationic metal ion in a sample, comprising:
   a) combining a compound of any one of claims 1-16 with a sample in an amount sufficient to generate a detectable fluorescent response to the metal ion;
   b) illuminating the sample to generate a fluorescence excitation or emission response; and
   c) observing the absorbance or emission response.

21. The method of claim 20 wherein a fluorometer, fluorescence microscope, laser scanner, flow cytometer is used to observe the absorbance or emission response.

22. The method of claim 20 wherein the polycationic metal ion is $Ca^{2+}$.

23. The method of claim 20 wherein the sample comprises living cells or biological fluids.

24. The method of claim 20, further comprising quantifying the fluorescence excitation or emission response.

25. The method of claim 20 wherein the compound exhibits a change in emission wavelength maximum upon binding to the polycationic metal ion.

26. The method of claim 20 wherein the compound exhibits a change in excitation wavelength maximum upon binding to the polycationic metal ion.

27. A kit for measuring the concentration of a polycationic metal ion in a sample comprising a compound of any one of claims 1-16.

28. The kit of claim 27, further comprising a component selected from a salt solution having biological osmolarity, a buffer, and a metal ion solution.

* * * * *